US012599689B2

(12) United States Patent
Stal et al.

(10) Patent No.: US 12,599,689 B2
(45) Date of Patent: Apr. 14, 2026

(54) SYSTEMS AND METHODS FOR STERILIZING GAMING EQUIPMENT

(71) Applicant: ARB LABS INC., Toronto (CA)

(72) Inventors: Alexander George Stal, Grimsby (CA); Andrzej Kepinski, Toronto (CA); Vlad Cazan, Thornhill (CA); Adrian Bulzacki, Mississauga (CA)

(73) Assignee: ARB LABS INC., Toronto (CA)

( * ) Notice: Subject to any disclaimer, the term of this patent is extended or adjusted under 35 U.S.C. 154(b) by 748 days.

(21) Appl. No.: 17/921,080

(22) PCT Filed: Apr. 26, 2021

(86) PCT No.: PCT/CA2021/050571
§ 371 (c)(1),
(2) Date: Oct. 24, 2022

(87) PCT Pub. No.: WO2021/212240
PCT Pub. Date: Oct. 28, 2021

(65) Prior Publication Data
US 2023/0173120 A1 Jun. 8, 2023

Related U.S. Application Data

(60) Provisional application No. 63/021,454, filed on May 7, 2020, provisional application No. 63/015,465, filed on Apr. 24, 2020.

(51) Int. Cl.
A61L 2/24 (2006.01)
A61L 2/10 (2006.01)

(52) U.S. Cl.
CPC .................................... A61L 2/24 (2013.01); A61L 2/10 (2013.01); A61L 2202/11 (2013.01);
(Continued)

(58) Field of Classification Search
CPC .......... A61L 2/24; A61L 2/10; A61L 2202/11; A61L 2202/121; A61L 2202/122; A61L 2202/14; A61L 2202/16; A61L 2/08
See application file for complete search history.

(56) References Cited

U.S. PATENT DOCUMENTS 7,397,041 B1 7/2008 Leonard
10,946,110 B1 3/2021 Colvin et al.
(Continued)

FOREIGN PATENT DOCUMENTS

CA 2090073 A1 8/1994
CN 204105626 U 1/2015
(Continued)

OTHER PUBLICATIONS

Arb Labs, "Safe Play", https://web.archive.org/web/20201203001528/https://arblabs.com/products-solutions/safe-play/, Dec. 3, 2020.
(Continued)

*Primary Examiner* — Maris R Kessel
*Assistant Examiner* — Aham Lee
(74) *Attorney, Agent, or Firm* — Norton Rose Fulbright Canada LLP

(57) ABSTRACT

A system and device for sterilizing gaming tokens stored in gaming equipment containers such as a tray having apertures for receiving gaining tokens in parallel rows. The system and device includes a sterilizing lid that can be positioned over a complementary tray having modular roller inserts inserted, the modular roller inserts operating in concert with the sterilizing lid to rotate the gaming tokens while the sterilizing lid emits a sterilizing light.

19 Claims, 35 Drawing Sheets

(52) U.S. Cl.
      CPC ... *A61L 2202/121* (2013.01); *A61L 2202/122*
                      (2013.01); *A61L 2202/14* (2013.01)

(56) References Cited

U.S. PATENT DOCUMENTS

| | | | |
|---|---|---|---|
| 2009/0252646 A1 | 10/2009 | Holden et al. | |
| 2010/0044852 A1 | 2/2010 | Cooper et al. | |
| 2011/0079732 A1 | 4/2011 | Kreitenberg | |
| 2011/0104004 A1* | 5/2011 | Bobbitt .................. | A63B 47/04 |
| | | | 422/186.3 |
| 2013/0256560 A1* | 10/2013 | Yerby ........................ | A61L 2/24 |
| | | | 250/455.11 |
| 2018/0256771 A1* | 9/2018 | Sinai ........................ | A63F 11/00 |

FOREIGN PATENT DOCUMENTS

| | | |
|---|---|---|
| CN | 204941154 U | 1/2016 |
| CN | 208974698 U | 6/2019 |
| JP | 2016101372 A | 6/2016 |

OTHER PUBLICATIONS

Canadian Intellectual Property Office (CIPO), International Search
Report and Written Opinion to PCT/CA2021/050571, Jul. 7, 2021.

\* cited by examiner

0:29

602

702B

702A

802

1000

| ITEM NO. | PART NUMBER | DESCRIPTION | -1 Standard QTY. |
|---|---|---|---|
| 1 | ARB-00159-1 | Roller Cover - Straight | 1 |
| 2 | ARB-00180 | AIM - SafePlay Module Cap v0.1 | 1 |
| 3 | ARB-00181 | SafePlay Roller - Standard | 2 |
| 4 | ARB-00184 | Roller Support Insert v0.3 | 4 |
| 5 | AIM GearBox 2 | | 1 |
| 6 | ARB-00177 | AIM SafePlay Config | 1 |
| 7 | ARB-00195 | AIM - Module Cap v0.1 | 1 |
| 8 | PCB mounting Bracket | SafePlay PCB Mount | 1 |
| 9 | 92000A015 | M3 x 8 PPH | 4 |
| 10 | 90910A762 | M1.6 x 6 PFH PSS | 1 |
| 11 | 99397A124 | M1.5PXx6.73H TPS | 2 |
| 12 | 94817A113 | | 0 |
| 13 | 91292A311 | M1.6X14 SHF | 2 |

| | ZONE | REV. | DESCRIPTION | DATE | APPROVED |
|---|---|---|---|---|---|
| REVISIONS | | A | NEW DOCUMENT | 2/11/2021 | |

1200

1600

1700

2000

2300

2302

2500

2700

2900

3100

3200

SYSTEMS AND METHODS FOR STERILIZING GAMING EQUIPMENT

CROSS-REFERENCE

This application claims all benefit, including priority to, and is a non-provisional of, U.S. Application No. 63/021, 454, filed 7 May 2020, and U.S. Application No. 63/015, 465, filed 24 Apr. 2020, both entitled Systems and Methods for Sterilizing Gaming Equipment, and incorporated herein by reference in their entireties.

FIELD

Embodiments of the present disclosure generally relate to the field of gaming equipment, and more specifically, embodiments relate to systems and methods for sterilizing gaming equipment.

INTRODUCTION

Gaming equipment, such as casino chips, is typically intended to be distributed and handled by customers. Circulated gaming equipment can attract, retain and spread various viruses and diseases from a single customer to multiple customers. However, gaming equipment is often irregularly shaped, difficult to separate, and includes various surfaces which are difficult to clean. Systems and methods for sterilizing gaming equipment in a safe, quick, convenient, intuitive, and/or automatic manner is desirable.

Presently, conventional approaches include applications of cleaning solutions with rags by staff, which is an undesirable solution as there is unnecessary game disruption and a requirement that a staff member interact with the gaming equipment, which may further the spread of disease.

This is particularly challenging in view of global pandemics, where spreading of viruses may be effected through contact surfaces.

SUMMARY

Gaming equipment, such as casino chips, is typically stored in purpose specific gaming equipment containers. The gaming equipment containers may comprise complex geometries to match the gaming equipment, making it difficult to integrate sterilization means which disinfect the complex geometries of the gaming equipment in the gaming equipment containers. In particular, the sterilization is desirable to be conducted in a minimally intrusive manner to avoid impacting the gaming experience. Moreover, gaming equipment containers are designed to hold gaming equipment in a compact manner, adding complexity to sterilizing the gaming equipment as there is limited available space.

Systems and method for sterilizing gaming equipment are discussed herein. Sterilizing gaming equipment can include, for example, sterilizing chips that are being held in a container, or placed in a position (such as in a betting spot on a gaming surface) where they are capable of receiving sterilizing light. Sterilizing, for the purposes of this application, means a reduction of the amount of living bacteria (e.g., various types of *Bacillus, Escherichia, Salmonella*, among others), fungus (e.g., *Aspergillius* types, *Penicillium* types), or virus (e.g., influenza, poliovirus) that can be present on the gaming equipment themselves. It does not need to be a full elimination as these approaches can be combined with other approaches to provide differing layers of safety.

A sterilization system is proposed that, in some embodiments, includes two complementary components, (i) a gaming equipment container (e.g., a dealer's chip tray or a cashier chip tray) that is adapted to receive or include roller actuators that can "roll the chips" along their circumferential edges when activated, and (ii) a complementary lid attachment having sterilizing light-emitters disposed therein to expose visible portions of the chips to the sterilizing light. When the complementary lid attachment is engaged onto the gaming equipment container, contact electronics, for example, may be utilized to complete an electrical circuit adapted to trigger the activation of the roller actuators to roll the chips. The contact electronics may transfer power, data (e.g., control signals), or both.

When the roller actuators roll the gaming objects or tokens (e.g., chips), the token edge surfaces are exposed over a period of time in an attempt to sterilize the tokens. To add exposure to the token top and bottom surfaces in addition to the token edge surfaces, in some embodiments, the tokens can include light transmitting layers such as front or bottom surface layers (e.g., clear acrylic, other UV-transparent materials), among others, such that light from the sterilizing light emitters is able to also penetrate the tokens and allow sterilization in between tokens as well on the top and bottom surfaces as well. For example, the tokens could include two external clear layers of materials that effectively sandwich a colored core of material such that when the light is provided to the tokens, the light is able to both cover the token circumferences as well as the top and bottom surfaces.

In operation, the complementary lid attachment is placed over the gaming equipment container by an individual or, if the complementary lid attachment is designed for permanent coupling with a particular gaming equipment container (e.g., a particular high volume or popular table), the actuation occurs for a period of time and the duration of time can be configurable depending on a desired level of sanitation. The complementary lid attachment can be utilized both at a dealer table at a gaming station, or also at other locations, such as trays used in cashier cages (prior to dispensing or accepting tokens and exchanging them for fiat currency). Accordingly, the tokens can be sterilized before or after contact (or periodically) to reduce a potential of transmission of contact-based illnesses.

In some embodiments, both a duration of time and a speed of rotation can be configurable, and machine operation characteristics can be provided to a table management system or other type of tracking backend to aid in tracking automatic compliance to desired cleaning protocols and sanitation levels. In another embodiment, compliance to desired cleaning protocols and sanitation levels can instead be simply shown through a coupled timer (e.g., a countdown timer for three minutes of cleaning) or a corresponding light or other type of signalling device coupled or proximate to the gaming equipment container (e.g., a light that shows a blue signal for clean, green signal for in play, a yellow signal for cleaning required soon, and a red signal for cleaning overdue).

Status indicators can be provided for when the unit is cleaning, and the status indicators may be physically present on the lid so that an operator (e.g., a cleaning professional who carries the lid around and cleans each tray) is able to observe status, or in another embodiment, an indicator message may be provided to a backend table management system that tracks various types of gaming information, such as loyalty points, wager amounts, cleaning status of various tables, among others.

When the yellow or red signal is shown, a staff member may bring over a complementary lid attachment and attach it for the pre-defined time-period such that the signal changes back to blue. In another embodiment, when the yellow or red signal is shown, the complementary lid attachment may be configured to automatically or upon receipt of a computing signal attach itself to the gaming equipment container and begin the cleaning cycle.

The gaming equipment container can include an open end where the tokens can be placed from the dealer, and the complementary lid can include the sterilizing light emitting source (e.g., LEDs configured for emitting UV-C light), and a surface which permits the sterilizing light to exit the device. The complementary lid device is designed to be positioned such that in operation, the surface at least partially encloses the open end of the gaming equipment container, and the sterilizing light emitted by the device passes through the open end of the gaming equipment container and sterilizes any gaming equipment stored within the gaming equipment container. In some embodiments, it may be important to avoid inadvertently exposing individuals to the sterilizing light.

The sterilizing light emitting source and the surface may be configured so that sterilizing light passes through the surface with uniform intensity across the entire surface, ensuring that any gaming equipment/gaming tokens (e.g., chips) within the gaming equipment container are sterilized. Sterilizing lights can include different types of wave-based sterilization, such ultrasonics, microwaves, and/or lasers. The complementary lid device may be portable, configured for use with multiple gaming equipment containers. For example, a single complementary lid may be brought to different tables and trays (e.g., carried there by cleaning staff), and attached on for a short period of time (e.g., during a break time or intermission, or simply when the associated table is less busy) for conducting a chip sterilization.

In example embodiments, a system for sterilizing gaming equipment includes a gaming equipment container for storing gaming equipment having at least one open end, and a device including a sterilizing light emitter. The device further includes a surface, and at least partially encloses the open end. The surface permits sterilizing light emitted by the sterilizing light emitter to enter the open end of the gaming equipment container to sterilize gaming equipment stored in the gaming equipment container.

The gaming equipment container may be retrofit or otherwise adapted for use with one or more modular roller units that are insertable at intervals. Each modular roller unit can be considered an "advanced insert module" (AIM), and can be a physical structural member configured to be placed in slots parallel to token stacks, and having sets of rollers disposed at intervals throughout to physically roll the tokens through frictional engagement (e.g., contact at a surface along the circumference of a circular token) of the rollers to the tokens as a drive element or motor engages or actuates the rollers to roll. There are different variations of the roller units as described herein and deviations are possible in accordance with some embodiments.

The modular roller units are not necessarily placed at every insertable space between apertures (spaces defined by tubes or other types of holding mechanisms). For example, modular roller units can be spaced out from one another such that each modular roller unit rolls the tokens in the two adjacent rows, and so on. In a non-limiting example, in a chip tray having twelve rows (and thus eleven slots therebetween), only six modular roller units may be necessary to be inserted, and other modular units can be inserted into other free slots to provide other types of capabilities. For example, other modular units can include sensor units for tracking a number of tokens in a token tube, communications units, among others. In another variation, for example, tray SKU can have 16 tubes, 15 slots, and the module positions (primarily concerning tubes 1 and 12 or (first & last) can be modified or adapted based on manufacturing decisions and complexity of execution, and additional slots can potentially be added.

There are technical challenges associated with ensuring smooth and durable operation of the system. In particular, in a gaming environment, the staff may handle the physical units roughly and the components and design should be hardened in anticipation of potential damage and inconsistent usage. Furthermore, from a manufacturing perspective, the tolerances associated with design compared to actual physical manufacturing may cause inconsistencies in dimensions that need to be accounted for in a practical implementation. Gaming tokens and surfaces contribute debris, accumulated dirt/oils (lotion on hands), and the tokens themselves may have physical damage, warping, manufacturing inconsistencies that can contribute to a failure to engage and rotate tokens. The systems described herein need to be durable and reliable to provide a long-lasting solution. As described herein, additional physical enhancements have been established on a number of variant designs of some embodiments in an attempt to improve the smooth operation of the system despite these technical challenges.

In practical usage, a number of different sizes of gaming tokens may be placed into the apertures, and these different sizes in addition to different shapes and made of different materials. For example, there may be chips having a diameter of 35 mm, 39 mm, 41 mm, 45 mm, and so forth. Accordingly, due to various chip diameters that may be desirable to accommodate, consideration of roller placement, protrusion offset, roller Diameter, manufacturing tolerances must be considered.

It is challenging to obtain a secure frictional engagement such that the chips can be properly rolled by the rollers, and in some embodiments, specific geometric configurations of the insert modules and/or the aperture tubes themselves are modified such that the contact point for the chips is at a modified position to improve the reliability and effectiveness of the system despite being used with different chip sizes (up to a practical limit of size differences—oversized tokens may fit and roll, but may limit 'normal operation' of the tray). As described herein, an example approach can include shaping certain edges to have elliptical portions (as opposed to circular portions) such that the sidewall of the tube defining the aperture or the insert coupling the roller prevents a "bottoming out of the chip". These types of issues can result in situations where there is reduced contact to the roller and accordingly, reduce friction such that the tokens cannot rotate properly. The tokens may end up being balanced on different points (e.g., high points or recessed low points) similar to how a lowered car on a speed bump, can get stuck on the bump and no amount of 'power' etc. from the wheels is able to move the car, short of external influence. The elliptical portions are intentional profile variations of the module walls to helps prevent points of contact that can 'hang' or incorrectly position the chips to improve the roller effectiveness.

In the proposed approach of some embodiments, the positioning of the rollers themselves on the roller modules may be specifically provided at a 9 o'clock or an 8:30 o'clock position, for example, as well to change a positioning of where the contact occurs, and to avoid debris being accumulated (e.g., if the roller was at a 6 o'clock position in the aperture, such as right in the bottom, debris, such as food, hair, oily films could accumulate in the well and prevent proper rolling action).

As the modular roller modules are consumable devices that are designed to be replaced over time as they are worn down, the wear level of the rollers needs to be managed and tracked, especially as contaminants and other foreign debris and objects are encountered in practical application. For example, even oil and lubricants from hands can build up over time and impact the functioning of the system, and it is not trivial to ensure that all of the tokens rotate, especially given practical inconsistencies in cost effective manufacturing and practical limitations on tolerances. As rollers are worn down, rollers become eccentric shaped and create problematic 'pulse' or 'indexed' rotation, where the chip only rotate a small amount, stops, then rotates again. Undesirable shaping may also result from manufacturing (e.g., bent axle when being made, causing concentricity of the rollers to axle, creating high/low areas, very much like a 'cam' or camming motion) or damaged (bending deformation) during install is the primary cause). The rollers can also be 'stripped, cut, shredded, worn, during use, in a manner that can cause 'cammed contact surfaces' compared to desired circular, round surface.

In another embodiment, the modular roller modules include computer processing capabilities provided on a coupled printed circuit board, and the modular roller modules are capable of obtaining load data through indirect monitoring of the speed at which an actuator is turning relative to the amount of power (e.g., current and/or voltage) provided to the actuator. Indirect monitoring, may include, for example, indirect sensing or sensor-less speed control (some of these methods are used for brushless motor control (BLDC), and some embodiments use brushed motors due to cost, but variants can also use BLDC motors if desired. BLDC motors also have more complicated electronic control systems). Other motors are possible, such as servomotors.

The load data can be tracked for assessing abnormal loading conditions, such as a load being too high or too low given a particular motor assembly type and/or expected loading of the tokens. In some embodiments, the load data is automatically utilized to determine that an error has occurred or an abnormal condition exists, and the system may be configured to automatically modify the actuation itself to account for the error, or in an attempt to fix the error (e.g., by rotating the roller in a backwards direction or opposite direction for a period of time to dislodge debris). Where the actuation has been modified, the duration of actuation of the corresponding sterilizing emission can be modified to ensure for additional time for sterilizing.

In some embodiments, the modular roller modules further include one or more sensors (e.g., optical sensors) that are adapted for tracking a load level corresponding to the corresponding aperture, which can operate in conjunction with a row detector. Variations include physically lifting the tokens (using sensory connected wires, bars, ribs, screws, spiral features, apertures for gas/liquid), or other sensors using lighting pipes or sources, ultrasonics, laser, among others.

Furthermore, the rotation of the chips can also allow the 'tubecount' token/chip scanner, etc. to increase its accuracy and reliability (precision of # of chips counted becomes more 'trustworthy' due to more 'unique surface exposure', (not only looking at the 'same surface'), and in some embodiments, the roller action is utilized to establish a second set of readings that can be utilized as a 'delta or difference' for comparison or ease of determination. In this example, if the count does not match between a pre-perturbed version and a perturbed version, there could be an accuracy issue that is flagged.

These sensors may return, for example, a "tubeCount" value. The controller may operate in conjunction with the "tubeCount" value to more accurately track loading conditions (e.g., different expected loads for different percentages of "fullness" of a particular tube of tokens).

In example embodiments, the device further includes an stabilizing part for partially enclosing the open end.

In example embodiments, the open end is defined by an edge, and the stabilizing part is a pad for mounting the device on the edge.

In example embodiments, the stabilizing part is two or more legs adapted to position the surface to at least partially enclose the open end.

In example embodiments, the device further includes a handhold or a plurality of handholds.

In example embodiments, the device further includes a battery connected to the sterilizing light emitter.

In example embodiments, the gaming equipment container further includes a power terminal or power terminals and the device further includes a receiving power terminal for interacting with the power terminal to power the sterilizing light emitter.

In example embodiments, the gaming equipment container further includes an actuator for displacing gaming equipment stored within the gaming equipment container. The actuator may be a motor, the gaming equipment container may further include a rolling pad, and the actuator may be configured to rotate the rolling pad to displace the gaming equipment stored within the gaming equipment container. The actuator may be a vibration machine, such as a haptic motor, using an eccentric rotating mass actuator (e.g., unbalanced weight attached to a shift). Other potential approaches include ultrasonics, linear vibro motors, haptic motors, etc.

In example embodiments, the device includes an attachment member or members for connecting to a lid of the gaming equipment container.

In example embodiments, the device is translucent and the device further includes a sterilizing light filter surrounding the sterilizing light emitter, the sterilizing light filter having an open end permitting sterilizing light emitted by the sterilizing light emitter to pass through to the surface.

In example embodiments, the sterilizing light emitter is bulb sterilizing light emitter. The bulb can be varied, for example, with a sterilizing light tube, CFL bulb, having various profiles, among others.

In example embodiments, the sterilizing light emitter is an LED sterilizing light emitter.

In example embodiments, the sterilizing light emitter emits sterilizing light in a uniform manner across the surface.

In example embodiments, the device further includes a timer in communication with the sterilizing light emitter for tracking a sterilization threshold.

In example embodiments, the device further includes a controller for selectively configuring the intensity of the sterilizing light emitter. The controller can be a physical controller circuit which provides machine interpretable instructions to control a power being delivered.

In some embodiments, the device further includes a controller for selectively configuring the type of sterilizing light emitted by the sterilizing light emitter.

In example embodiments, the device further includes a controller for selectively configuring the actuator.

In example embodiments, the device further includes a switch or switches for selectively deactivating the sterilizing light emitter.

In an aspect, a method for sterilizing gaming equipment includes at least partially enclosing an open end of a gaming equipment container with a surface of a device including a sterilizing light emitter, the surface permitting sterilizing light emitted by the sterilizing light emitter to pass through the surface into the open end, and activating the sterilizing light emitter for a sterilization duration to sterilize gaming equipment stored in the gaming equipment container.

In example embodiments, method includes stabilizing the device includes adjusting a stabilizing part of the device in relation to the gaming equipment container.

In example embodiments, the open end is defined by an edge, the stabilizing part is a pad for mounting on the edge, and method includes stabilizing the device includes mounting the pad and the edge.

In example embodiments, the stabilizing part is two or more legs adapted to vary the orientation of the surface, and method includes adjusting the two or more legs to align the surface with the open end.

In example embodiments, the gaming equipment container further includes an actuator, and method includes further includes actuating the actuator of the gaming equipment container to displace gaming equipment within the gaming equipment container.

In example embodiments, the actuator includes a motor and a rolling pad, and the method further includes actuating the motor to rotate the rolling pad to rotate the gaming equipment stored within the gaming equipment container. In example embodiments, method includes actuating the motor for a sterilization duration.

DESCRIPTION OF THE FIGURES

In the figures, embodiments are illustrated by way of example. It is to be expressly understood that the description and figures are only for the purpose of illustration and as an aid to understanding.

Embodiments will now be described, by way of example only, with reference to the attached figures, wherein in the figures:

In FIG. 12, example component types are also illustrated.

DETAILED DESCRIPTION

Figure 1:
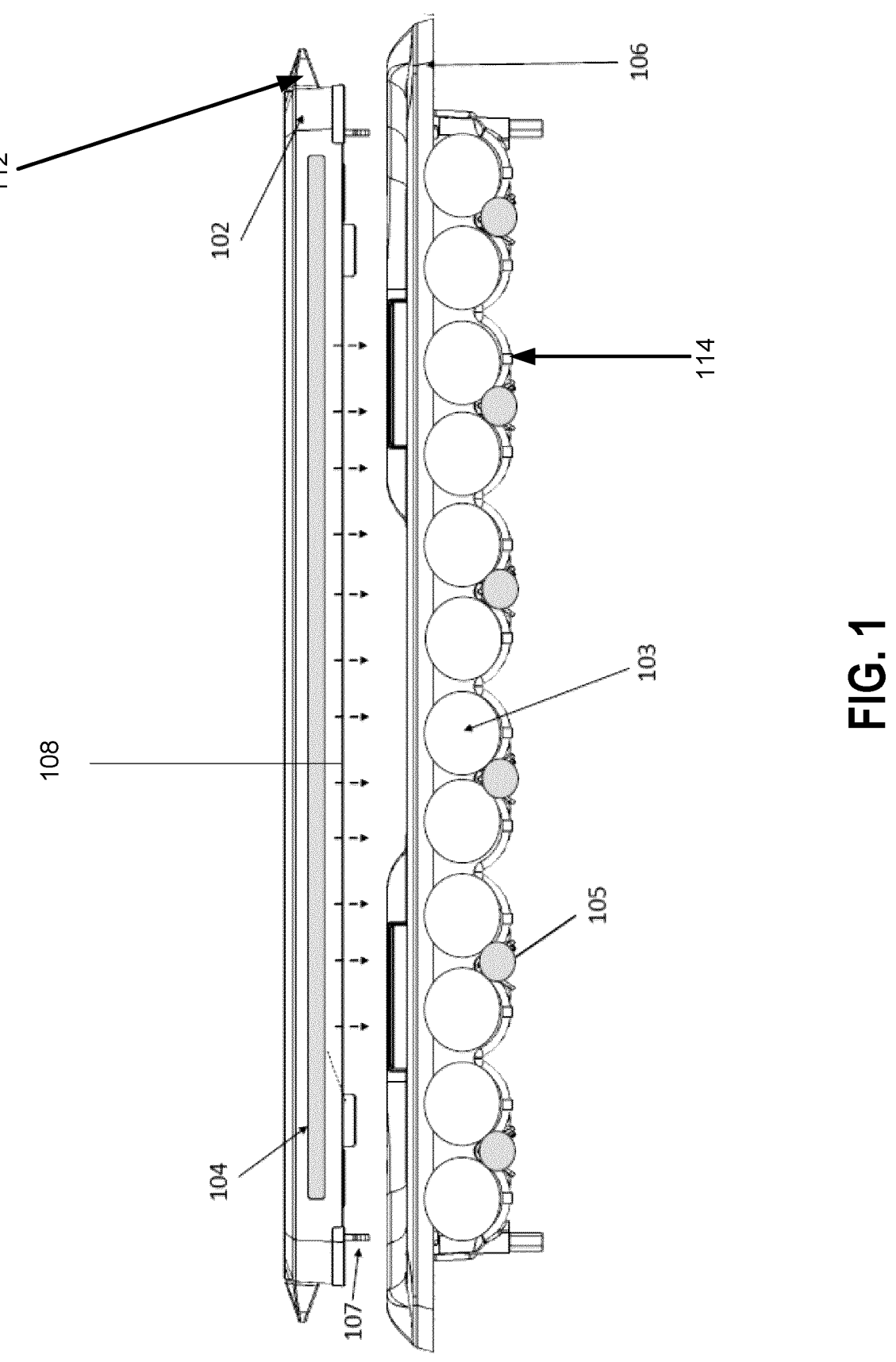
FIG. 1 is a side view of a system for sterilizing gaming equipment containers, according to an example embodiment.

A challenge with gaming tokens is that they are handled often by different individuals during the course of a gaming session, for example, where the tokens represent bet markers that are traded between players or between players and a dealer during the course of a gaming event.

Gaming tokens are placed, for example, in marked regions of a gaming table or gaming surface to indicate a particular bet or wager being placed, and can be carried around by individuals as markers of their returns, to be obtained or traded in at a cashier to be converted into fiat currency. In the course of a particular gaming session, the gaming tokens are stored in gaming equipment container (e.g., a dealer's chip tray) when not in play.

Systems and methods for sterilizing gaming equipment while they are disposed within the gaming equipment container are discussed herein, along with specific practical and technical problems encountered during implementation and proposed approaches to address these practical and technical problems.

A sterilization system is proposed that, in some embodiments, includes two complementary components, (i) a gaming equipment container (e.g., a dealer's chip tray) that is adapted to receive or include roller actuators that can "roll the chips" along their circumferential edges when activated, and (ii) a complementary lid attachment having sterilizing light-emitters disposed therein to expose visible portions of the chips to the sterilizing light. In operation, the complementary lid attachment is placed over the gaming equipment container by an individual or, if the complementary lid attachment is designed for permanent coupling with a particular gaming equipment container (e.g., a particular high volume or popular table), the actuation occurs for a period of time and the duration of time can be configurable depending on a desired level of sanitation. The gaming equipment container need not be a dealer chip tray on a table. For example, the gaming equipment container may be a tray in a special sterilizing area where used trays are sterilized along with their tokens, or used in a cashier cage where the trays are sterilized prior to the tokens residing within being converted to or from fiat currency.

When the complementary lid attachment is engaged onto the gaming equipment container, contact electronics, for example, may be utilized to complete an electrical circuit adapted to trigger the activation of the roller actuators to roll the chips. The contact electronics may transfer power, data (e.g., control signals), or both.

When the roller actuators roll the gaming objects or tokens (e.g., chips), the token edge surfaces are exposed over a period of time in an attempt to sterilize the tokens. To add exposure to the token top and bottom surfaces in addition to the token edge surfaces, in some embodiments, the tokens can include light transmitting layers such as front or bottom surface layers (e.g., clear acrylic, polycarbonate), among others, such that light from the sterilizing light emitters is able to also penetrate the tokens and allow sterilization in between tokens as well on the top and bottom surfaces as well. For example, the tokens could include two external clear layers of materials that effectively sandwich a colored core of material such that when the light is provided to the tokens, the light is able to both cover the token circumferences as well as the top and bottom surfaces.

Sterilizing, for the purposes of this description, means a reduction of the amount of living bacteria, fungus, or virus that can be present on the gaming equipment themselves. It does not need to be a full elimination as these approaches can be combined with other approaches to provide differing layers of safety. Applicant has conducted various tests using dosimeters and research into specific exposure amounts required for sterilization for different types of use cases (e.g., molds, viruses, bacteria). In a specific example, covid-19 is similar to SARS viruses, which requires ~10-20 mJ/cm^2 with direct UV-C @ 254 nm. This achieves 99.9% disinfection (in laboratory settings). A practical approach, for example, involves using 1000-3000 mJ/cm^2 to ensure that rate. A challenge with sterilizing with UV-C light however, is that there may be a tendency to damage component finishes (e.g., bleaching them). The required time for a UV dose can change, for example, based on distance and exposure strength. For example, as described further herein, some tokens are residing in a recessed aperture having a slope relative to neutral, and thus some tokens in the row are closer to the emitter source and some are further from the emitter source.

The gaming equipment stored in the gaming equipment container may be manipulated to expose various surfaces of the gaming equipment to the sterilizing light. In example embodiments, the gaming equipment is manipulated with an actuator which rotates the gaming equipment, exposing various surfaces of the gaming equipment. In example embodiments, the actuator is a vibrating machine, which vibrates the gaming equipment container such that it rotates or displaces the gaming equipment and exposes various surfaces of the gaming equipment.

In another embodiment, the actuators are provided in the form of plurality of modular roller devices that are insertable and configured to be positioned between (i) two adjacent parallel rows of cylindrical gaming tokens or alternatively, (ii) an adjacent parallel row of cylindrical gaming tokens and a sidewall of the gaming token tray. In another embodiment, the modular roller devices are instead adaptable into the sidewall.

The plurality of modular roller devices can be inserted such that each of the plurality of modular roller devices is adapted to handle two adjacent parallel rows such that all rows of tokens in use are adjacent to at least one of modular roller device so that when the system is activated, all of the tokens disposed therein in the apertures is rolled. The amount of tokens being received in a particular aperture need not be fixed. For example, in some embodiments, some tubes are extendible such that they do not have set token counts. For example, there may be 12 parallel rows of apertures that receive cylindrical gaming tokens, and accordingly, 11 cavities for insertion of modules. 6 roller modules in this scenario would be sufficient, each roller module having opposed rollers on either side to be able to roll the tokens on the adjacent rows, respectively. In a variation, a roller module may only have a roller on one side and not the other—in this variation, the roller module is adapted for insertion between a sidewall of the gaming token tray and an aperture (e.g., on an edge) such that there is only one side being adjacent to a row of gaming tokens.

In example embodiments, the device includes an attachment member to connect to existing gaming equipment containers, allowing for retrofitting of existing systems. The device is attached to the existing gaming equipment containers, and a timer may indicate that a sterilization duration has been completed.

Referring now to FIG. 1, a device 102 and a gaming equipment container 106 are shown. In the shown embodiment, the gaming equipment container 106 is a chip tray including chips 103 (e.g., cylindrical gaming tokens), stored within a bed for chips within the chip tray gaming equipment container 106. In example embodiments, the gaming equipment container 106 is a bin or tray which stores chips and dice. In further example embodiments, the gaming equipment container 106 is a transparent tray for storing chips, such as a tray used to transport chips from a casino cage to a gaming floor. The gaming equipment container 106 can also store 'clear markers/spacers' used for security purposes, and dealer ease of use, either evenly interspaced or 'on top' of some of the chips.

Figure 6:
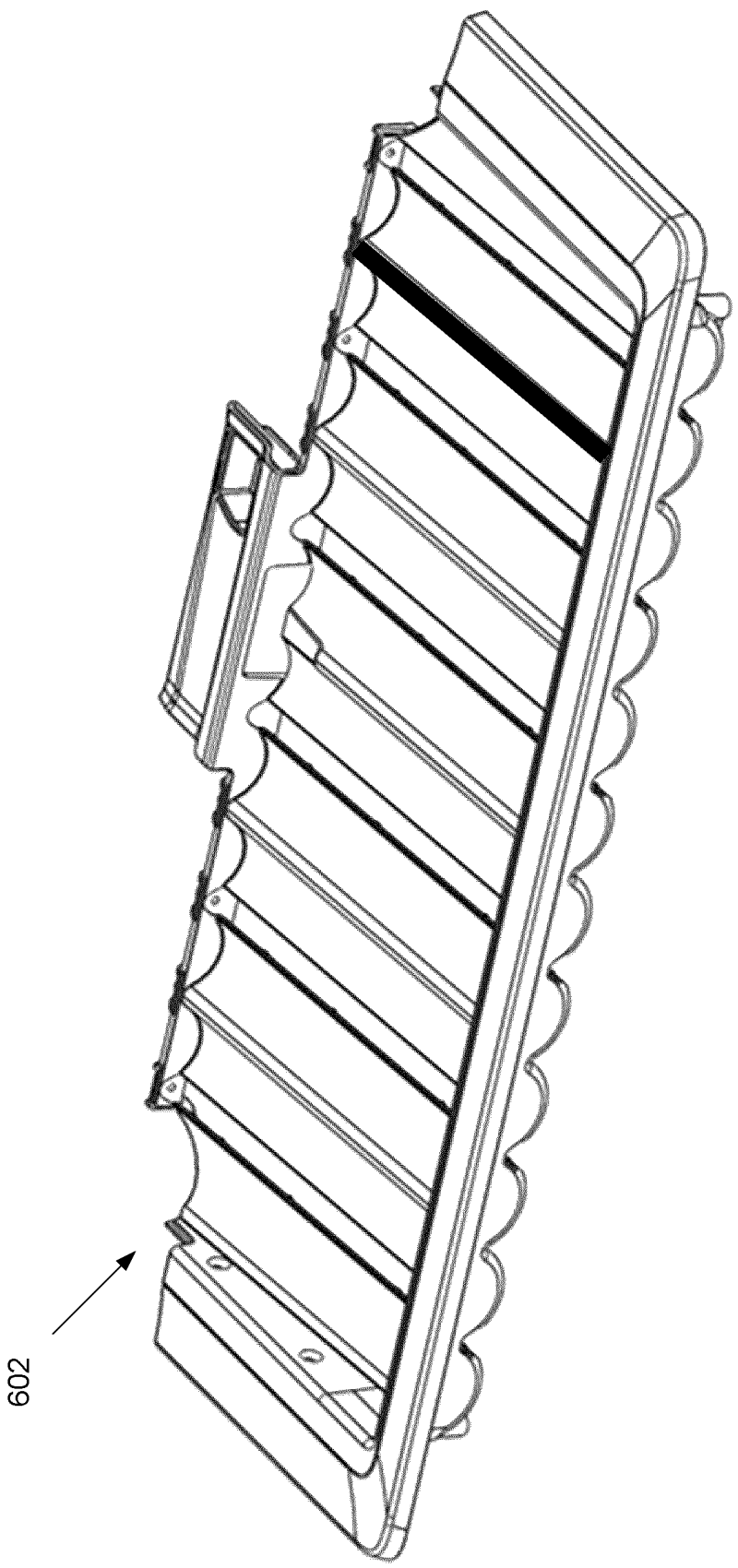
FIG. 6 is a perspective view of an example gaming equipment container, according to some embodiments.

The gaming equipment container 106 includes an open end 602, for example as shown in the chip tray gaming equipment container 106 embodiment shown in FIG. 6. The open end 602 permits sterilizing light to pass through and become incident on the surface of any gaming equipment stored in the gaming equipment container 106. The open end 602 may be any size or shape, limited to a single surface or span multiple surfaces of the gaming equipment container 106, or otherwise.

In another embodiment, a tray lid device 102 is shown that is adapted for complementarily couple (e.g., fit overtop of the dealer tray such that an electrical contact or contacts or a physical trigger such as a plunger is connected (valve, switch, solid state switch)) with the dealer tray such that the tray lid device is able to detect or determine that it is coupled to the dealer tray. When the tray lid is coupled, for example, through the completion of an electrical contact or circuit (e.g., a circuit loop), power can be provided to the tray lid device 102, which can be configured to begin a sterilizing cycle by causing the sterilizing light to be adduced for a period of time. An activation signal may be established (or if the connection is broken, a de-activation safety signal). In some embodiments, the duration of the period of time is automatically adjusted based on operating characteristics or conditions relating to the dealer tray or the actuation of actuator devices therein (e.g., a load capacity of the tray indicating how many tokens are located therein, a zone indicator indicative of which zones of tokens have been interacted with, motor load characteristics). This information may be augmented for accuracy through other sensors, such as optical sensors for tracking accurately a number of tokens in a tube aperture, for example.

The device 102 includes a sterilizing light emitter 104 (e.g., an ultraviolet (UV) light source, such as UV-C light source which may emit light at between 200-300 [nm], or other emissions wavelengths) a for emitting sterilizing light 110. In example embodiments, the sterilizing light emitter 104 includes a single tube bulb which emits sterilizing light. In some embodiments, for example, the sterilizing light emitter 104 includes a LED sterilizing light emitter. In example embodiments, LED-based sterilizing light emitters are utilized to increase the lifecycle of the device 102 due to an increased longevity of LED-based emitters. In some embodiments, inexpensive single tube sterilizing light bulbs are used for each of replacement.

Figure 4:
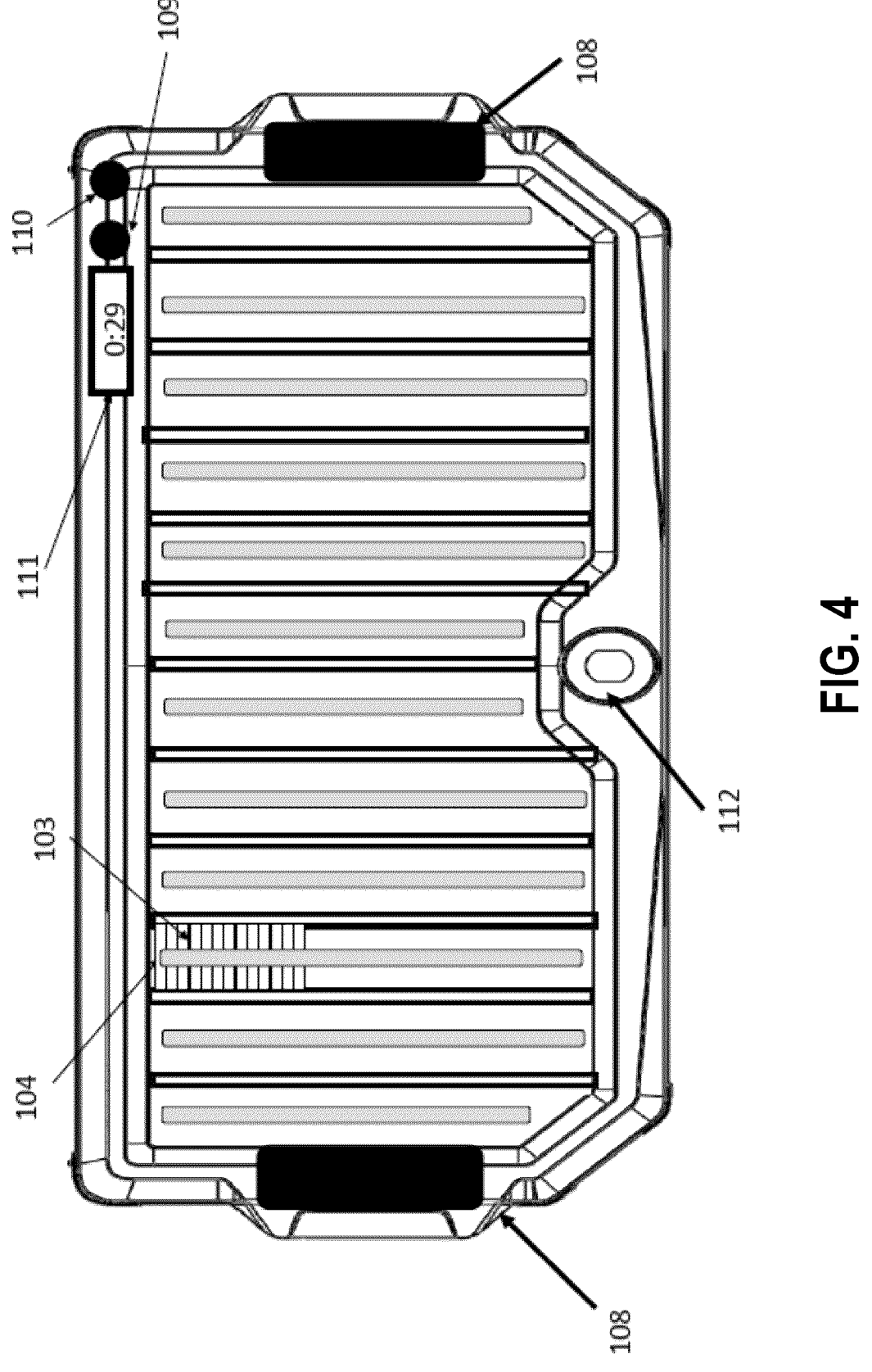
FIG. 4 is a top view of a further example device for sterilizing gaming equipment, according to some embodiments.

The device 102 may comprise various numbers or combinations of sterilizing light emitters 104. Hereinafter, the sterilizing light emitter 104 will be referred to in the singular for ease of reference. One possible arrangement of the sterilizing light emitter 104 includes, as shown in FIG. 4, includes 12 LED strips, one for each chip tube in a chip tray gaming equipment container 108, each of the LED strips located in the middle of each of the chip tube.

The device 102 further can include a surface 108 which permits sterilizing light 110, emitted by the sterilizing light emitter 104, to pass through. The surface 108 in the embodiment shown is the is rectangular and sized to permit sterilizing light 110 to pass the entirety of the open end 602 of gaming equipment container 106 and interact with all chips in the gaming equipment container 106. In example embodiments, the surface 108 is any shape or size.

The surface 108 may be the same size as the open end 602 of the gaming equipment container 106. In example embodiments, the surface 108 covers part of the open end 602, and the device 102 is moved across parts of the open end 602 until the surface has traversed the entire open end 602.

The surface 108 and the sterilizing light emitter 104 may be arranged such that the light intensity emitted by the sterilizing light emitter is uniformly distributed across the entire surface of the gaming equipment container.

Figure 5:
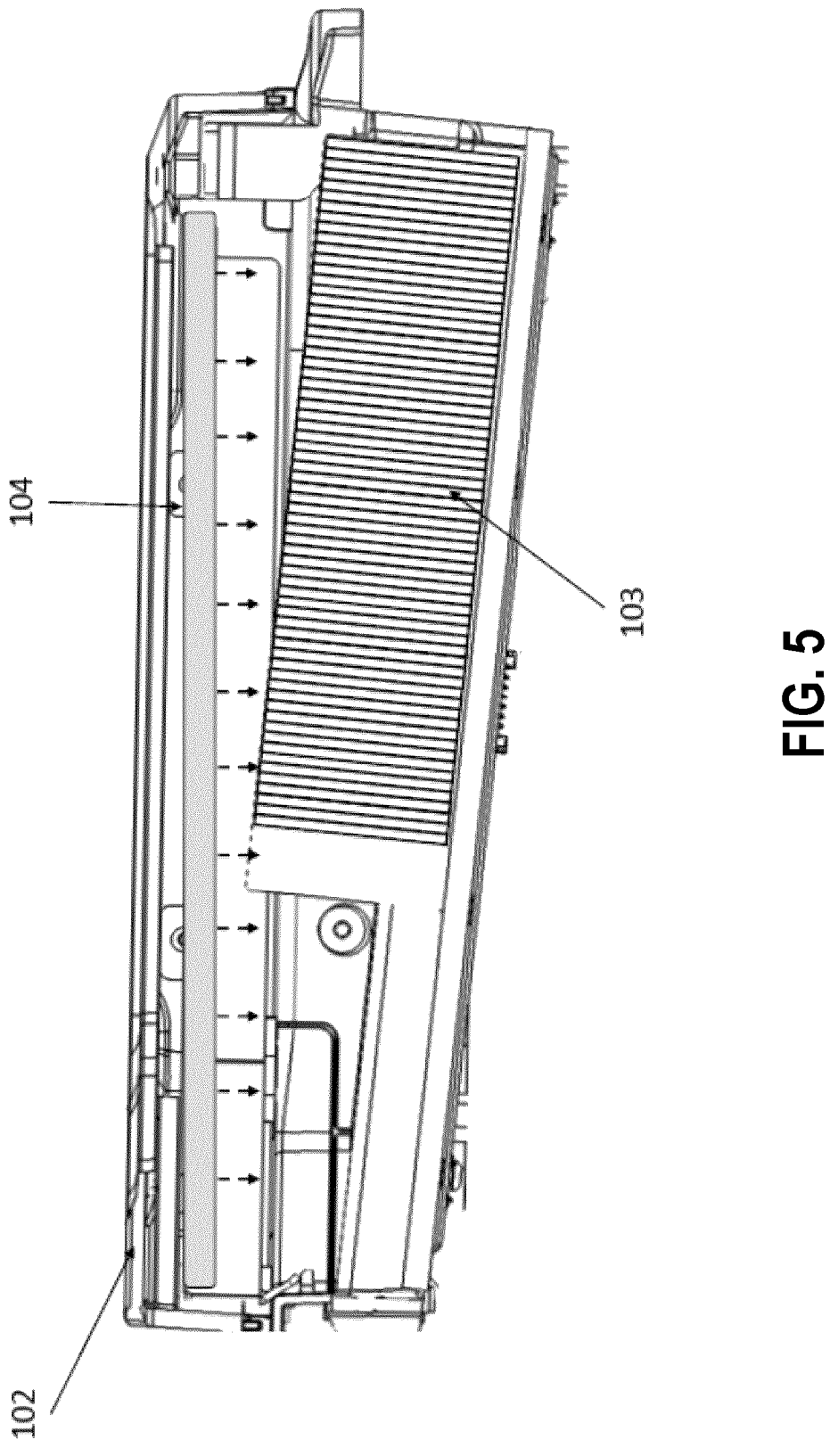
FIG. 5 is a side view of a device for sterilizing gaming equipment, according to some embodiments.

In example embodiments, the surface 108 and the open end 602 of the gaming equipment container 106 are parallel to one another. In some embodiments, for example as is shown in FIG. 5, the surface 108 and the open end 602 of the gaming equipment container 106 are not parallel to one another.

The sterilizing light emitter 104 may be configured to adjust intensities within the device 102 to account for a surface 108 and open end 602 of the gaming equipment container 106 relative position to ensure that sterilizing light of uniform intensity is incident upon the gaming equipment in the gaming equipment container 106. For example, device 102 may adjust sterilizing light emitter 104 to have LEDs further away from the open end 602 of the gaming equipment container 106 operate with an increased intensity. The sterilizing light need not be of uniform density in all embodiments. While uniform intensity/dosage rate could be implemented using zoned/segmented UV emitters, non parallel targets/sources are also possible and result in intensity disparity based on proximity. Closer means that there is a higher dosage rate, smaller AOE (Area of effect), and further means that there is less dosage rate, larger AOE.

According to at least one aspect, the gaming equipment container 106 is a cash box having at least one open end for receiving cash, the device 102 is a lid for the cash box, and the sterilizing light emitter 104 of the device 102 emits sterilizing light into the open end of the cash box.

Figure 34:
Figure 34:
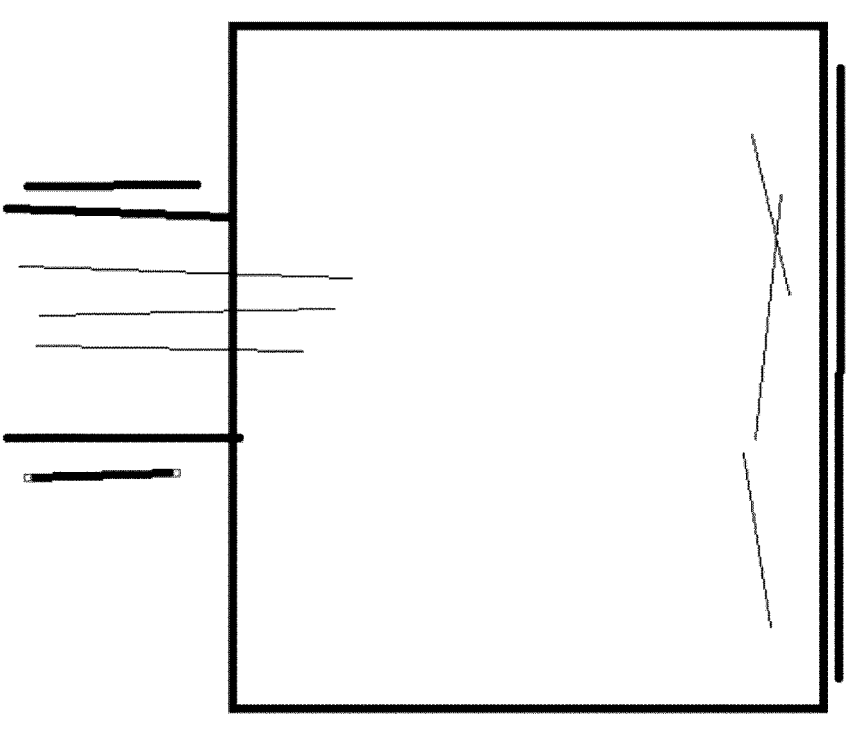

In example embodiments, the gaming equipment container 106 is a cash box, and the sterilizing light emitter 104 of the device 102 is emitted to the bottom of the cash box gaming equipment container 106 to clean money as it dropped into the cash box gaming equipment container 106. As a result, any cash within the cash box gaming equipment container 106 that has any bacteria or virus material on it may be cleaned while in the cash box. It may be that, when the cash box is opened to collect the cash, any cash within the cash box gaming equipment container 106 is already disinfected. This example is shown in FIG. 34, which is a diagram 3400 showing how bills could be agitated. The emitter, for example, may reside on a 'bottom' of the container. In another variation, the system may emit doses of sterilizing light, when money is deposited, for example, as single or only a few bills at a time, with a very high dosage of UV to be effective (sub <2 s). In the drawing 3400, the box shown is the container, emitters are provided on the bottom and 'throat' (2× or encompassing) at point of money insertion, and the thin lines represent money.

In example embodiments, the device is located within the cash box, and the sterilizing light emitter 104 of the device 102 is located on a wall or surface of the cash box, and emits sterilizing light into the cash box.

In example embodiments, the device 102 further comprises a stabilizing part for stabilizing the device 102 in relation to the gaming equipment container 106. For example, in the embodiment shown, the stabilizing part is an edge of the surface 110 which stabilizing part allows the device 102 to act as a lid for the gaming equipment container 106. In example embodiments, the stabilizing part is a series of protrusions in the edge of the surface 110 for an interference fit with coupling parts in the gaming equipment container 106.

The stabilizing part may be two or more legs adapted to position the surface over the open end 602. The device 102 can be placed on top of the equipment gaming container 106, rest on the surface of the equipment gaming container 106, or protrude a sealing part to interface with the equipment gaming container 106, with legs on each of the corner of the device. The legs may have wheels connected to them to allow the device to roll.

The stabilizing part may further include a locking mechanism 112. In the example embodiment shown in FIG. 2 and FIG. 3, the locking mechanism 112 is a cam lock for fastening the device 102 to the gaming equipment container 106.

The gaming equipment container 106 may further include an actuator 105 for displacing the stored gaming equipment therein. For example, in the embodiment shown, the device 102 comprises an actuator including a roller pads 105 and a motor (not shown), for rotating the roller pads 105. The roller pads 105 can be positioned to protrude the equipment gaming device 108 and contact with the gaming equipment stored within the gaming equipment container 106 (e.g., chips). When the roller pads 105 are actuated, contact with the chips will rotate the chips.

The actuator may include any number of motors and any number of roller pads. In example embodiments, a single motor, connected to a belt which is connected to a plurality of roller pads and the motor simultaneously rotates the plurality of roller pads. In some scenarios, for example, each roller pad is connected to a separate motor, and the roller pads may be independently operated at various speeds, or may be synchronized.

In example embodiments, the surface of the roller pads 105 is made from a rubber like material that provide traction when touching the gaming equipment, getting them to spin. The roller pads 105 may be actuated to spin slowly to avoid losing tracking with the gaming equipment.

In example embodiments, the actuator 105 continues to displace the gaming equipment until a full sterilization is complete. Alternately, the actuator 105 may be configured to displace the gaming equipment in stages, for example rotating the chips 90 degrees, stopping, then rotating the chips again until sterilization is complete, namely the chips complete one full 360-degree cycle.

In some embodiments, the actuator 105 is a vibration machine configured to vibrate at a threshold frequency. For example, the vibration may include a motor with an unbalanced mass will spin at a set speed to create a vibration along the gaming equipment container. This vibration will cause the chips in the container to start rotating in their slot. The vibration machine may be configured to stop after a predetermined amount of time, when all the chips are expected to have rotated a full 360 degrees, a predetermined about of vibrations, and so forth.

According to some embodiments, for example, the device 102 may include a handhold, such that the device is manually positioned above the open end 602. This device will have a handle allowing the user to lift it up by hand and wave it across the gaming equipment container or may place it overtop the gaming equipment container and remove it when the sanitization process is completed.

The device 102 may include a battery 108. The battery 108 may be operably connected to and power the sterilizing light emitter 104, a timer, or any other powered component of the device 102.

In example embodiments, the battery 108 is removable. According to some embodiments, the battery 108 may be charged wirelessly. For example, where the device 102 is used to retrofit existing gaming equipment container 106 lids, the device 102 may include a wirelessly charging battery which may ease the retrofitting process.

Figure 2:
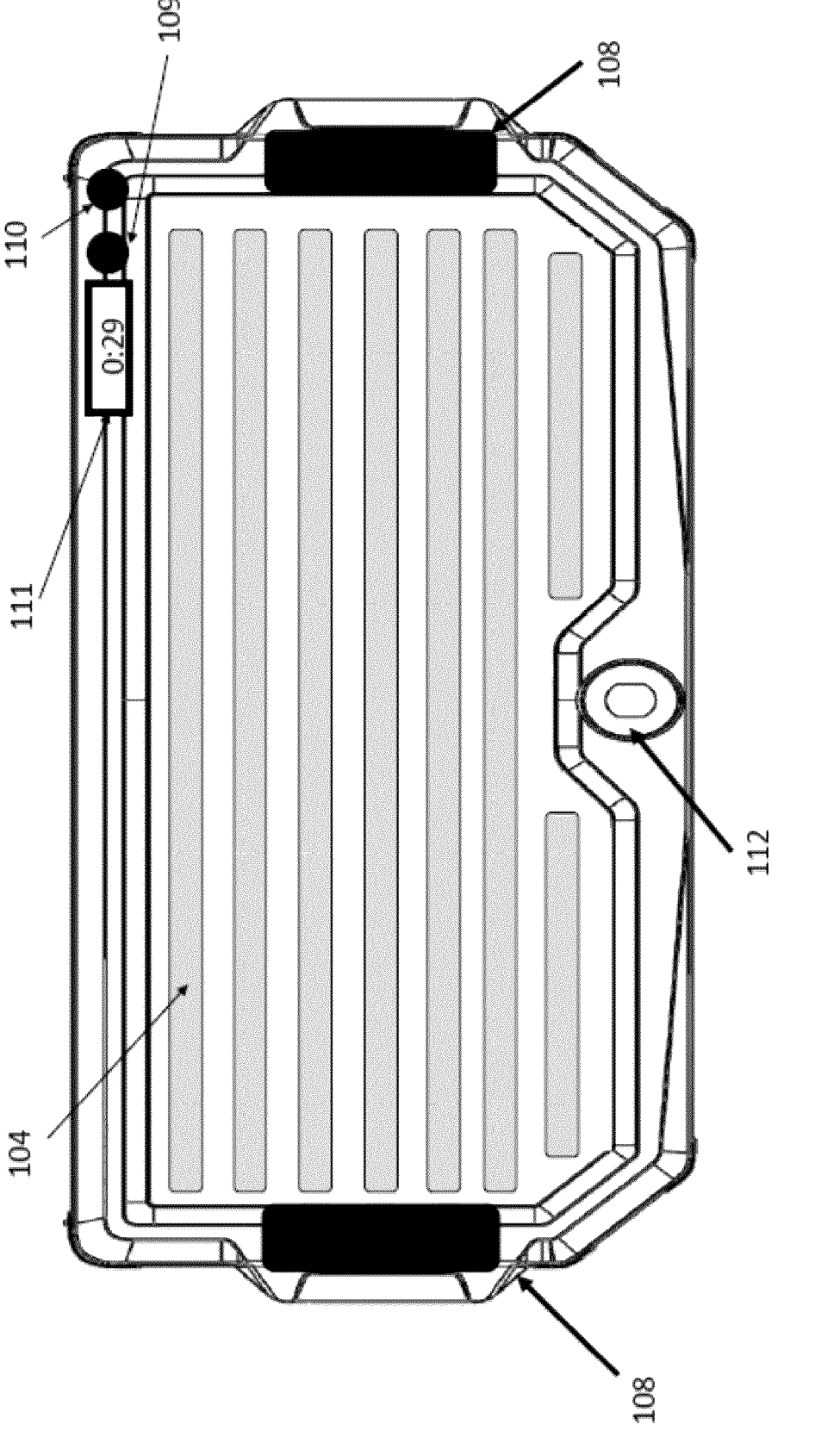
FIG. 2 is a top view of a device for sterilizing gaming equipment, according to some embodiments.
Figure 3:
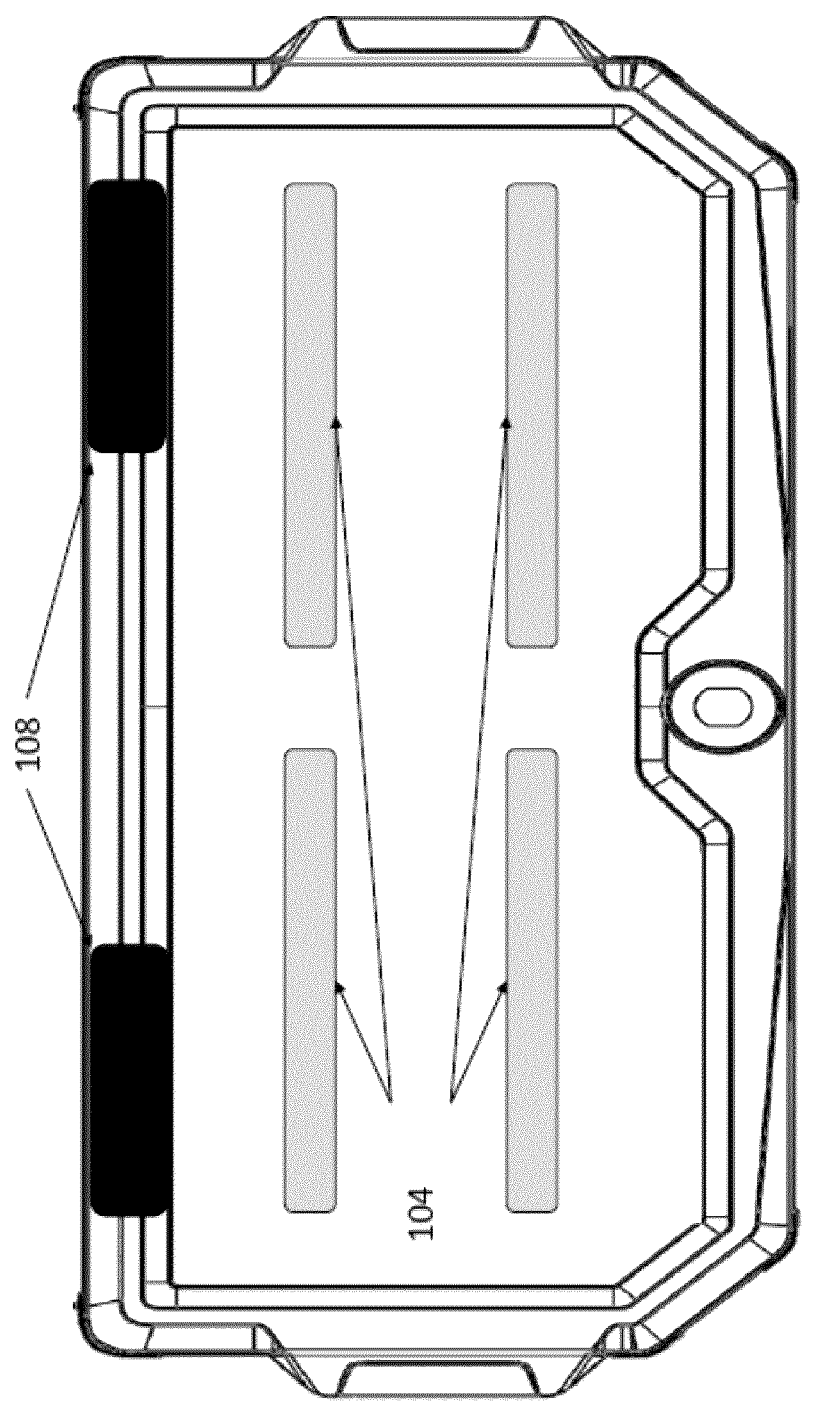
FIG. 3 is a top view of an example device for sterilizing gaming equipment, according to some embodiments.

The device 102 may include multiple batteries 108, as shown in FIG. 2. In example embodiments, the device 102 includes any combination of amount, size, and type of battery 108 located anywhere within or on the device 102.

The device 102 may include a receiving power terminal 107, operably connected to powered components within the device 102, for receiving power. For example, in the embodiment shown in FIG. 1, the device 102 includes a receiving power terminal for receiving power from the gaming equipment container 106. A terminal plug a male/female matching pair can be embedded to both the gaming equipment container 106 and the device 102 so that when the device 102 is placed over the gaming equipment container 106 the connectors can mate and power is connected. Contact points (e.g., two) on the gaming equipment container 106 can be used to provide power to the device 102.

The receiving power terminal 107 may be integrated into the stabilizing part, as shown in FIG. 1, or in some embodiments, the receiving power terminal 107 may be a separate part of the device 102. In example embodiments, the power terminal 107 includes a wire with a connector that could be plugged in manually to power the device.

Similarly, in example embodiments the gaming equipment container 106 may be battery powered or powered by a receiving power terminal.

The device 102 may include an attachment member (not shown) for connecting to an existing gaming equipment container 106 lid as a means of retrofitting existing gaming equipment container 106 systems. For example, the device 102 may be attached to a gaming equipment facing surface of the existing gaming equipment container 106 lid, with the surface 108 facing the gaming equipment. The attachment member of the device 102 may connect with the existing gaming equipment container 106 lid based on magnetic (e.g., magnets which attract to a metallic lid, or adhesive magnets which are attached to the existing gaming equipment container 106 lid and the device 102), snap fit connectors, screw connectors, adhesive connects, etc.

The device 102 may be translucent to comply with casino gaming regulations, or security requirements, which require the chips being visible when the open end 602 of the gaming equipment container 108 is closed. For example, device 102 may be made from a translucent plastic.

In example embodiments, the device 102 further includes a sterilizing light filter (not shown). In an example, embodiments, the sterilizing light filter is translucent, surrounds the sterilizing light emitter 104 and has an open end 602 permitting sterilizing light emitted by the sterilizing light emitter 104 to pass through to the surface 108. For example, the sterilizing light filter may be a coat applied to interior surfaces of the device 102 surrounding the sterilizing light emitter 104. In example embodiments, the device includes at least in part a transparent glass window and the sterilizing light filter may protect the dealers and customers eyes.

The device 102 may include a timer 111, in communication with the sterilizing light emitter 104, for tracking activation of the sterilizing light emitter 104. For example, the timer 111 may be configured to provide an alert (e.g., an alert sound, alert display notification on a display, etc.) after the sterilizing light emitter 104 has been activated for a duration sufficient to sanitize the gaming equipment in the gaming equipment container 106.

In example embodiments, the timer 111 includes a display, as shown in FIG. 2, and the amount of time remaining until sterilization is displayed. Any type of display is contemplated.

The timer 111 may be operably connected to a battery (e.g., battery 108), or the timer 111 may be connected to and receive power only when the sterilizing light emitter 104 is powered.

In some scenarios, the device 102 includes an intensity controller. The controller may allow for selectively configuring the intensity of the sterilizing light emitter 104. For example, in the embodiment shown, the controller may be a knob 109 for adjusting the intensity of the sterilizing light emitter 104.

The intensity controller may be configured to decrease light intensity where, for example, the sterilizing light emitter 104 is expected to be activated for extended periods of time when the gaming equipment is not in use. The intensity controller may increase the light intensity of sterilizing light generated by the sterilizing light emitter 104 to decrease a sterilization duration, for example where cleaning needs to be done in a short amount of time.

A sterilization duration may be based on the length of time between cleaning cycles. For example, where a cleaning cycle has not been activated in an extended period of time, the sterilization duration may be increased to account for possible increased biological materials deposited on the gaming equipment. In some embodiments, the sterilization duration is based on the type of gaming equipment. For example, cards may be more like to accumulate biological materials in comparison to casino chips. The sterilization duration may be based on the intensity, of wavelength of the sterilization light emitted.

In example embodiments, the sterilization duration is based on the speed of an actuator 105. For example, the sterilization duration may be based on the gaming equipment being actuated a sufficient time to ensure a threshold number of gaming equipment surfaces have been exposed to the sterilizing light.

In some scenarios, the device 102 includes a wavelength controller for selectively configuring the type of sterilizing light emitted by the sterilizing light emitter 104. For example, the wavelength controller may be a knob (not shown) for adjusting the wavelength of the light emitted by the sterilizing light emitter 104. The wavelength controller may vary the wavelength of sterilizing light generated by the at sterilizing light emitter 104 during a cleaning cycle, which may be more effective than a cleaning cycle including only one wavelength of sterilizing light.

In example embodiments, the device 102 includes a switch controller for powering the device 102 on and off. For example, in the shown embodiment in FIG. 2 the switch is an on/off button, configured to deactivate the sterilizing light emitter 104.

The device may comprise any combination of controllers, which may be battery powered or externally powered, and so forth.

In example embodiments, the device 102 includes a logic controller for controlling the powered components of device 102. For example, a controller may be configured to automatically adjust the intensity of the sterilizing light emitter 104 with the intensity controller based on a remaining battery power.

In example embodiments, the logic controller adjusts the intensity of the sterilizing light emitter 104 based on a time the sterilizing light emitter 104 is active. The logic controller may run on different "programs", for example a high speed cleaning (90 seconds of high intensity sterilizing light), a standard clean cycle (300 seconds medium intensity sterilizing light), overnight cleaning (24 hour light intensity sterilizing light).

In example embodiments, the logic controller is configured to shut down the sterilizing light emitter 104 after a threshold activated duration to ensure the longevity of the sterilizing light emitter 104. For example, the logic controller may turn off the sterilizing light emitter 104 after a 12 hour cycle to prevent the sterilizing light emitter 104 from operating all the time.

In some embodiments, for example, the logic controller automatically powers the sterilizing light emitter 104 upon sensing power being received by the receiving power terminal 107, commences the timer 111 based on a sterilization threshold, and deactivates the sterilizing light emitter 104 once the sterilization threshold has been reached.

The device 102 may further comprise a fan (not shown), in order to drive air out of the gaming equipment container 106 during the operation of the sterilizing light emitter 104 to promote heat dissipation.

Self-Sterilizing Material

According to one or more aspects of the current disclosure, a self-sterilizing gaming container is disclosed. The self-sterilizing gaming container can be used independently of a system for sterilizing gaming equipment described in FIGS. 1-6. In example embodiments, the self-sterilizing gaming container is used as the gaming equipment container (e.g., gaming equipment container 106) in the system for sterilizing gaming equipment described in FIGS. 1-6. Any combination of the self-sterilizing gaming container and the systems and methods for sterilizing gaming equipment is contemplated.

In some embodiments, for example, the self-sterilizing gaming container can be a casino chip tray, chip tray rack, playing card shoe, die holder, card discard rack.

Self-sterilizing gaming containers include at least a first part made from self-sterilizing material. In some embodiments, the self-sterilizing gaming containers are coated with self-sterilizing material. Self-sterilizing materials include any one of, or any combination of, or any alloy of aluminium, antimony, arsenic, barium, bismuth, boron, copper, gold, lead, mercury, nickel, silver, thallium, tin, zinc. In example embodiments, the self-sterilizing material is an aluminum alloy with copper particles.

Self-sterilizing materials, for example heavy metals like copper, have an oligodynamic effect which kills or destroys viruses, fungicides and bactericides and prevents growth of these. When the surface of an object comes into contact with these materials, they can become sterile after a period of time.

According to example embodiments, the first part of the self-sterilizing gaming containers are the surfaces of the self-sterilizing gaming containers. For example, the surfaces of the self-sterilizing gaming containers may be made of copper, or an alloy containing copper, such as an aluminum alloy with copper particles.

Figure 8:
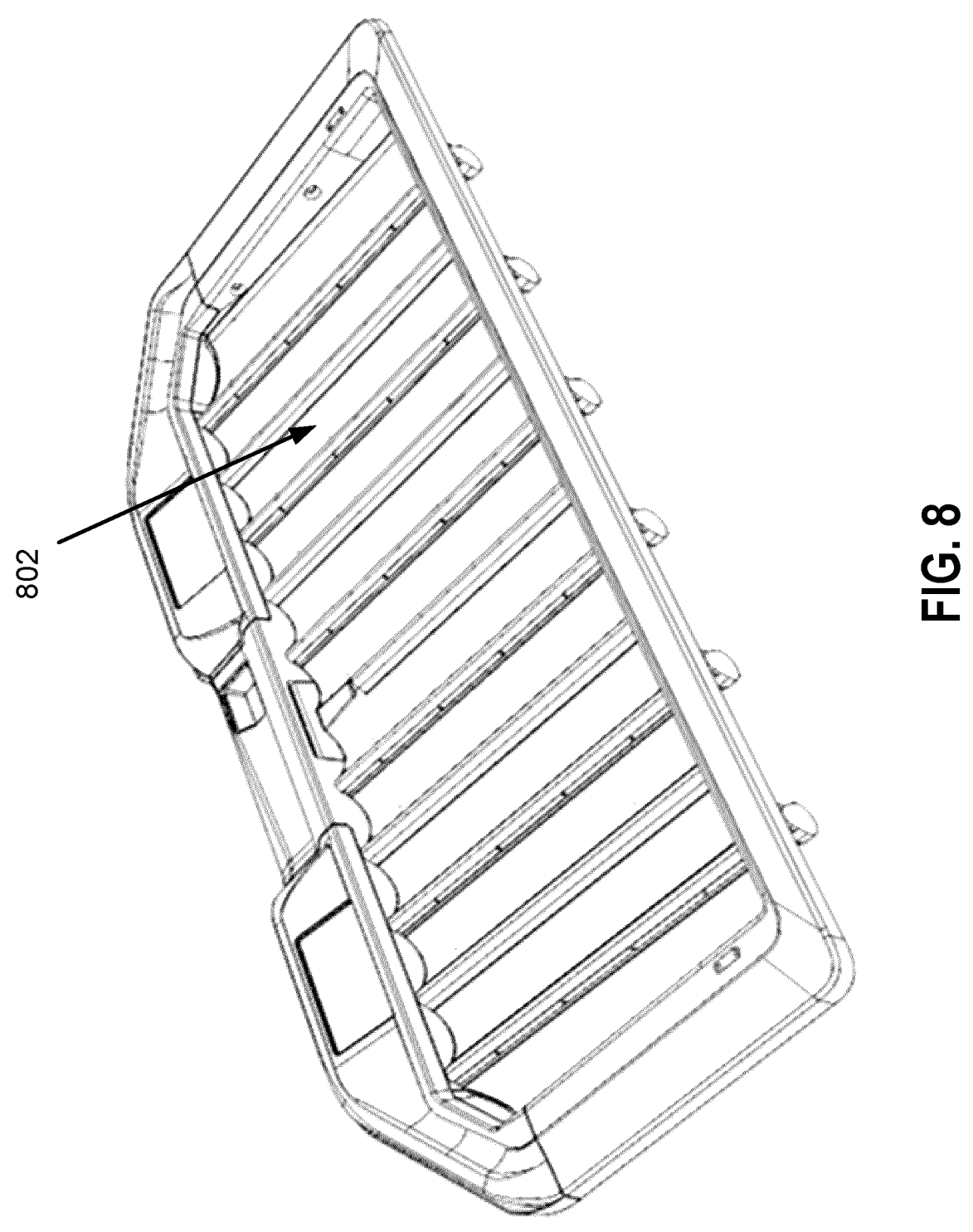
FIG. 8 is a perspective view of a further example gaming equipment container made at least in part of self-sterilizing material, according to some embodiments.

In some scenarios, the first part of the self-sterilizing gaming containers can be a strip of material within the container. FIG. 8 shows a casino chip tray with indicator 802 pointing at the self-sterilizing chip retaining contour. According to some embodiments, for example, only the bottom strip of the chip retaining contour may be made of copper, or an alloy containing copper, such as an aluminum alloy with copper particles, being the most likely surface that the chips will touch. When chips are placed on and make contact with this surface, they may become sterilized.

Figure 7:
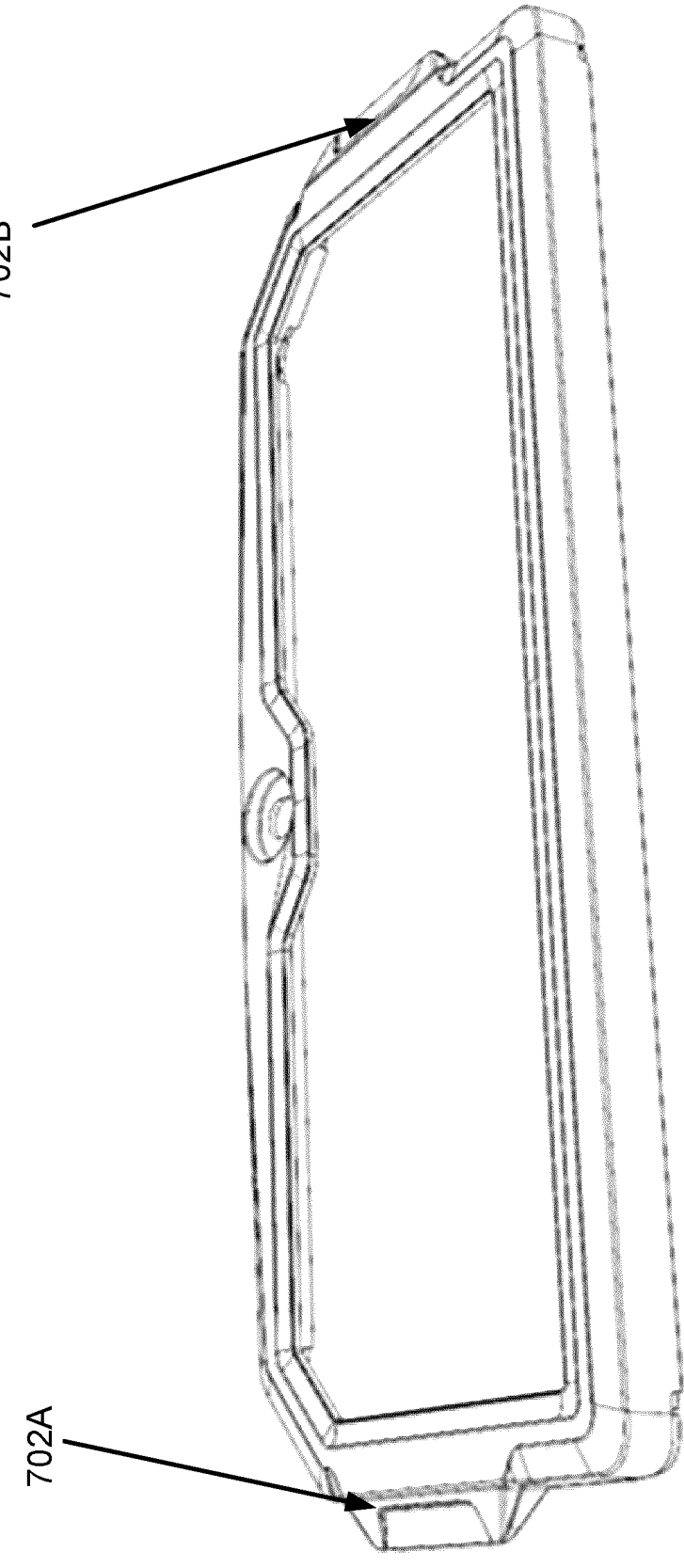
FIG. 7 is a perspective view of an example gaming equipment container made at least in part of self-sterilizing material, according to some embodiments.

In example embodiments, as shown in FIG. 7, the self-sterilizing gaming container is a chip tray lid with the lid handles 702A made out of, or coated with, a copper, or an alloy containing copper, such as an aluminum alloy with copper particles. In example embodiments, only the lid handles 702A of the self-sterilizing gaming container chip tray lid made out of, or coated with, a copper, or an alloy containing copper, such as an aluminum alloy with copper particles.

In example embodiments, the self-sterilizing gaming containers is a gaming equipment container (e.g., gaming equipment container 106) for storing gaming equipment having at least one open end, and is connected to an actuator (e.g., actuator 105) for displacing gaming equipment stored within the gaming equipment container. In example embodiments, at least part of the actuator (e.g., actuator 105) can be made at least in part from self-sterilizing material. For example, where the gaming equipment container is a casino chip tray, and the actuator is a chip roller, as shown in FIG. 1, the gaming equipment container can be fully lined with a self-sterilizing material, be made out of self sterilizing material or contain an section or area of the surface with self-sterilizing material. An actuator can move the gaming equipment over the surface area with the self-sterilizing material to sterilize the equipment.

In example embodiments, the system for sterilizing gaming equipment (e.g., the system described in FIGS. 1-6) includes gaming equipment containers 106 which are self-sterilizing gaming containers. For example, a casino chip tray gaming equipment containers 106 with a device 102 that is positioned so that the lighting emitter is facing the casino chips and the casino chip tray gaming equipment containers 106 is made out of a self sterilizing material.

The system for sterilizing gaming equipment (e.g., the system described in FIGS. 1-6) can include gaming equipment containers 106 which are self-sterilizing gaming containers made from any one of, or any combination of, or any alloy of Aluminium, Antimony, Arsenic, Barium, Bismuth, Boron, Copper, Gold, Lead, Mercury, Nickel, Silver, Thallium, Tin, Zinc.

According to some embodiments, any one of, or any combination of, the elements of the system for sterilizing gaming equipment, such as the gaming equipment container 105, the device 102, and the actuator 106 for displacing gaming equipment stored within the gaming equipment container 105, include at least some part or coating made from self-sterilizing materials.

In example embodiments, a self sterilizing liner is used in combination with any one of, or any combination of, the elements of the system for sterilizing gaming equipment, such as the gaming equipment container 105, the device 102, and the actuator 106 for displacing gaming equipment stored within the gaming equipment container 105. For example, a self sterilizing liner made of copper, or a copper alloy, can be attached to the bottom of a chip tray gaming equipment container 105 with a device 102 sterilizing the top part of chips within the chip tray, and the self sterilizing liner sterilizing the bottom part of chips within the chip tray.

In example embodiments, only a surface layer of any one of, or any combination of, the elements of the system for sterilizing gaming equipment, such as the gaming equipment container 105, the device 102, and the actuator 106 for displacing gaming equipment stored within the gaming equipment container 105, is made from self-sterilizing materials. For example, a card discard rack can be made to have a copper or copper alloy surface.

In example embodiments, the self-sterilizing portion of any one of, or any combination of, the elements of the system for sterilizing gaming equipment, such as the gaming equipment container 105, the device 102, and the actuator 106 for displacing gaming equipment stored within the gaming equipment container 105, is removable. For example, a self-sterilizing liner made of copper may be removably connected to the device 102 handles.

Reference is made throughout the following to sterilizing gaming equipment or sterilizing light. It is to be understood that the term sterilizing is intended to capture any degree of germ, virus, bacterial, etc. (the "Biological Materials"), removal or termination and that the term is not limited to complete elimination or even substantial removal or termination of the Biological Materials.

Figure 9:
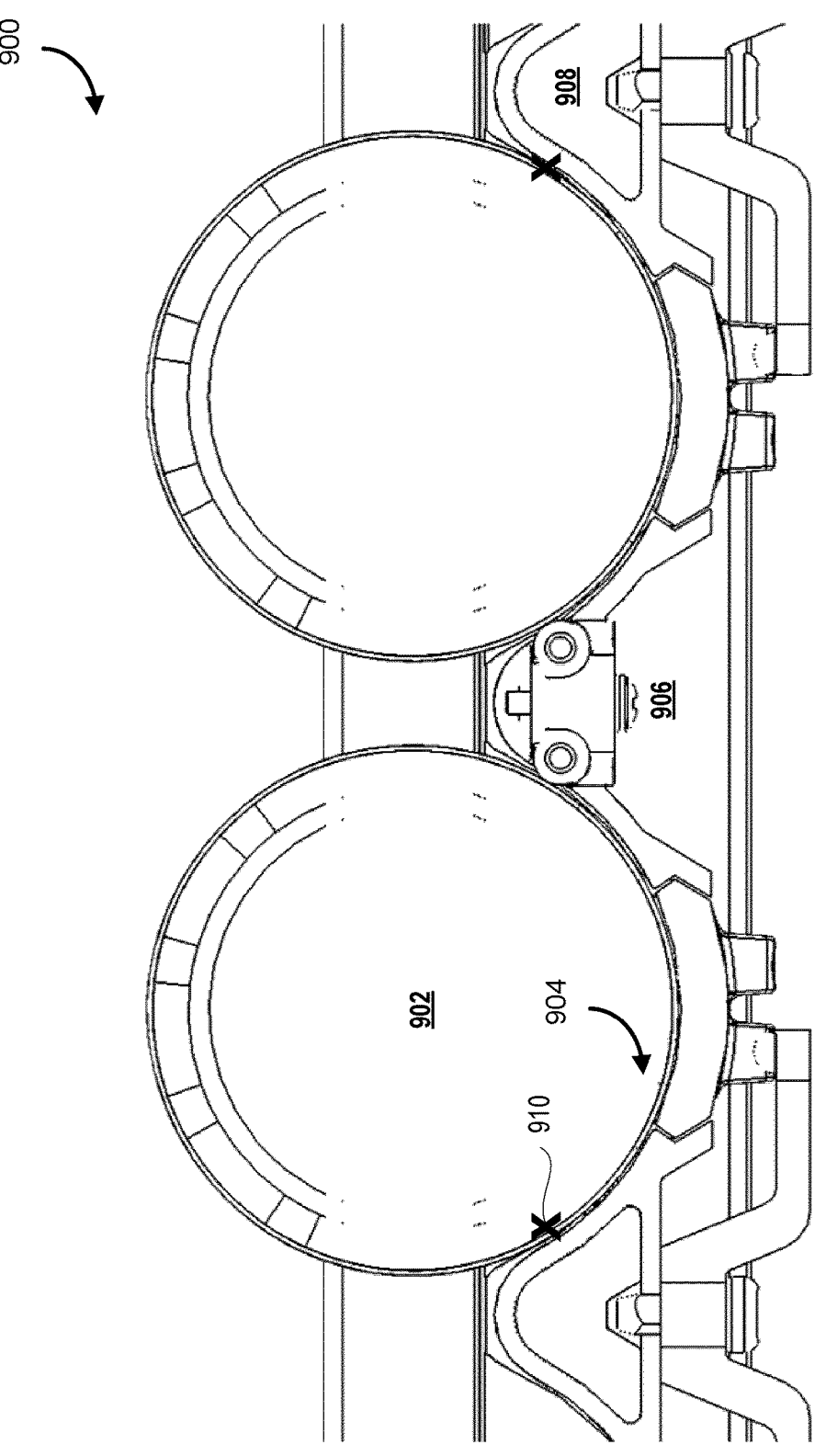
FIG. 9 is a cross-sectional view of one or more apertures holding cylindrical gaming tokens in parallel rows, according to some embodiments. A modular roller insert is shown positioned between adjacent apertures.

FIG. 9 is a cross-sectional view 900 of one or more apertures holding cylindrical gaming tokens in parallel rows, according to some embodiments. A modular roller insert is shown positioned between adjacent apertures.

A cylindrical gaming token 902 resides within an aperture 904 formed by a tube of a gaming token tray, each tube receiving rows of cylindrical gaming tokens 902. Tokens 902 can include, 'pucks' physical money vouchers, gaming coins, gaming disks, among others. It is important to note that the cylindrical gaming tokens 902 may be of different shapes and sizes, as the actual tokens being used by a particular establishment may change over time and a diversity of different types of tokens can be utilized for denominating different values (e.g., $1, $5, $25, $100, $500, $1000), among others. These tokens can have different diameters, and this diversity in diameters specifically can be challenging for the roller sterilization system described herein to handle, and specific modifications are proposed in some embodiments.

A modular roller device insert 906, and this variation of the modular roller device insert 906 is positioned adjacent to two apertures that hold parallel rows of tokens. The modular roller device insert 906 can also have a variant that is one-sided having a single roller (e.g., where modular roller device insert 906 is against a sidewall).

In this example, it is important to note that modular roller device insert 906 is not necessarily inserted into every insert location. In this example, another type of module 908 is staggered in intervals with modular roller device insert 906 to provide other types of modular functionality, such as a tube counting mechanism having optical sensors disposed in intervals along a perpendicular axis adapted to track a number of chips in each aperture and their locations, and in a further embodiment, the tube counting mechanism can also include on-board processors and memory to track changes in the number of chips in each aperture (e.g., as tokens are used for gaming, the size of the stacks increases and decreases). The token contacts a sidewall at 910 as a contact point against which the token is rotated against. The module 908 can be modified to further increase reliability with 'protrusions', shaped profiling, to better enact desired function of adjacent AIM units.

The 'contact point' or interface point, can be also be protruded or exaggerated from the surface to help alleviate rolling engagement issues (forces the roller to be its secondary contact point as opposed to other less useful points Chip diameter can also be made nearly irrelevant unless its oversized per the design parameters.

As described further in this description, in some embodiments, additional information obtained from other modules or sensors are further utilized to modify the sterilization operation of the system described herein.

The rollers contact sidewalls of the tokens and cause the adjacent cylindrical gaming tokens (e.g., tangentially incidental) to rotate through frictional engagement. The modular roller device insert 906 includes controllable actuators (e.g., motors and corresponding gear assemblies) that are powered by a power source that rotate the rollers through the application of torque. When the sterilizing lid is attached, the sterilization cycle can begin, and the tokens 902 are rotated (ideally at least having one full rotation) such that the sidewalls or circumferential faces are exposed to a sterilizing light.

When a duration of time has elapsed or the lid is removed, the sterilizing cycle can end and/or the actuators may be controlled to stop operation. In some embodiments, the actuators are also configured to undertake debris cleaning cycles whereby the rollers are controlled to operate in various directions in accordance to a cleaning pattern (e.g., forwards, then backwards, then forwards again) in an attempt to dislodge undesirable materials stuck in the roller assembly. If there are abrupt removal indicating an uncontrolled or unintentional removal of the lid, additional safety features may be initiated to stop the emission of the sterilizing light. The cleaning cycle can be manually implemented, for example, to allow for the manual running of a cleaning cycle.

If a cleaning cycle occurs during a sterilization cycle, additional time may be added to the sterilization cycle to account for time required for the cleaning cycle. In the course of a single cleaning cycle, the token may be rotated for a number of rotations at a speed that is calibrated for reducing wear and to increase longevity of the roller or the actuator. In some embodiments, an additional wear cycle may be caused where the roller simply rotates a pre-defined rotation to modify a contact point with tokens residing with the aperture. The wear cycle may not necessarily be dependent on the cleaning or sterilization cycle, and for example, can use external data to govern cycle event frequency.

Figure 10:
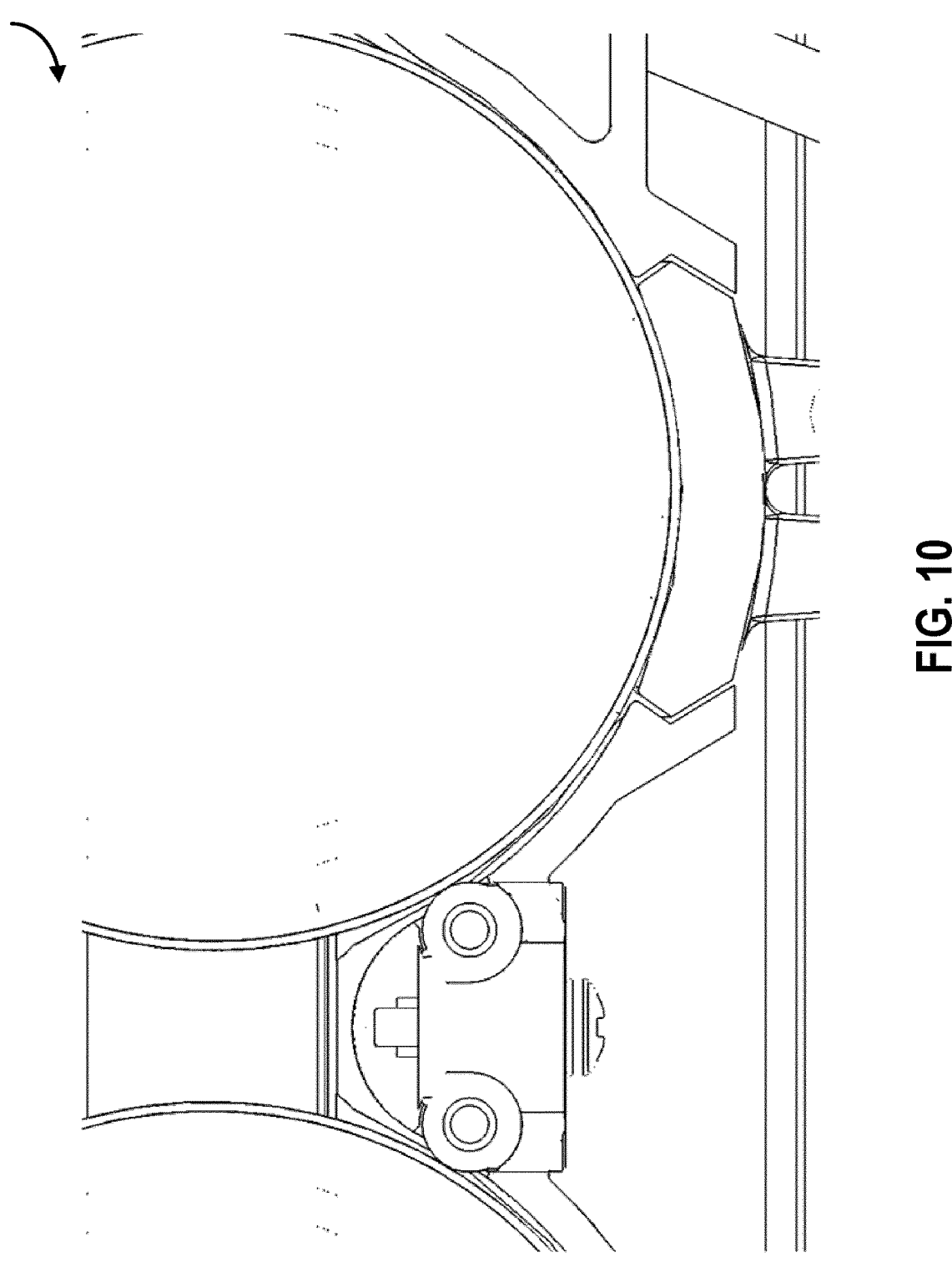
FIG. 10 is an enlarged view of the modular roller insert, according to some embodiments.

FIG. 10 is an enlarged view 1000 of the modular roller insert, according to some embodiments. In this drawing, a smaller diameter token is shown that has many surface area points for contact with the sidewalls of the tube defining the aperture.

Figure 11:
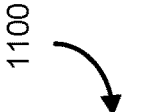
FIG. 11 is an exploded view of the modular roller insert, according to some embodiments.
Figure 11:
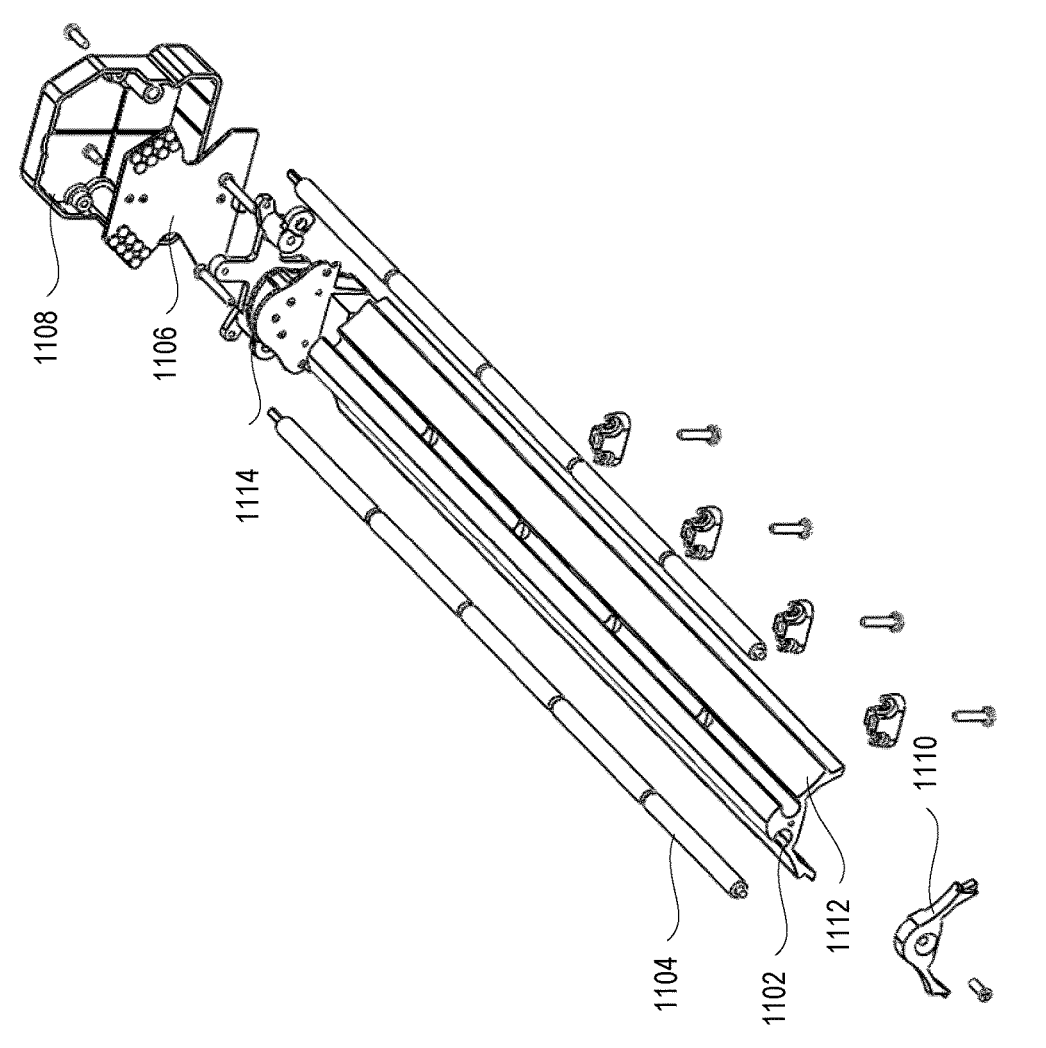

FIG. 11 is an exploded view 1100 of the modular roller insert, according to some embodiments. In this view, the modular roller insert can include a central housing 1102, which has grooves and slots therein to include corresponding roller 1104, which can be disposed either on one side or both sides of the central housing 1102. The roller 1104 can be supported by a roller support that may include an optional spacer to prevent additional friction or abnormal/excess wear on rollers.

In another embodiment, the roller 1104 is configured for telescoping action through the use of an extending actuator (e.g., hydraulic, pneumatic) whereby the rollers are capable of being retracted and extended within the primary profile. In this example, the roller 1104, in addition to rotational motion, is capable of a limited amount of translational motion extending from the modular roller insert housing towards a token. The extending actuator variation is useful in reducing wear damage during normal use and aids with enforcing 'positive roller contact' (no longer relying on gravity to ensure chip rotating). The extending actuator can include, for example, springs, motor, actuator, linear motor, weights, linkages, slides, gears etc., among others, and are configured to include a hard stop mechanism to prevent over extension of the rollers.

A extending roller can operate based on the token diameter, extending until contact within its range (for example, an extension range could be ~2-7 mm, and can be adapted to various positions to be passively or actively loading/force/dynamic/weight to create friction/contact/incidence with the chips. In an active loading example, the approach may include utilizing actuator, motor, solenoid, linear driver, gears, linkages, etc. to maintain a 'load, sensor input, PID loop, feedback reference, etc.) to maintain forced contact with chips, thereby ensuring 99%+ of chips roll. In the passive loading example, a spring, weight, weighted linkages, gravity or other approaches are utilized to create forced contact with the chips, and may require a 'lock' to keep rollers from popping out and interfering with tray use (due to low volume of chips keeping them in).

The modular roller insert is insertable into a corresponding slot in the gaming tray between parallel tubes defining the apertures in which the gaming tokens can reside within. A circuit board 1106 is coupled to an endcap 1108 housing which includes structural features to mate and/or securely couple with the gaming tray such that the modular roller insert is securely positioned during operation. An endcap 1110 can be utilized to secure the rollers in place. Snap constraints can also be utilized to that prevent the unit from sliding out if the tray is moved, and these may also help with 'seating' or passive positioning the AIM unit within the tray's rails.

When the roller 1104 is activated, a frictional engagement is established with the gaming token and the roller 1104 rotates, rotating the adjacent token. The roller 1104 is actuated with a sufficiently large torque to be able to rotate the adjacent token. The roller also has additional 'mechanical advantage' due to size disparity of the chips, beyond the roller's initial torque capacity. For example, 40 mm chip vs a 4 mm roller yields a 0.1:1 ratio (10 rotations of roller=1 rotation of chip).

The circuit board 1106 can include one or more processors, on-board memory, and instruction sets for controlling an actuator module 1114, which can include a motor, gear assemblies, among others, which are used to controllably rotate the rollers 1104. The circuit board 1106, in some embodiments, is configured to control operating characteristics of the rollers actuator module 1114, for example, by controlling an amount of power (e.g., by controlling a voltage or a current amount) that is provided to rotate the rollers 1104. The circuit board 1106 can also be configured to track an operating speed of the rollers 1104 (e.g., rotations per minute) which can then be combined with the power provided to determine load data that can be extrapolated to identify, for example, roughly an estimated number of tokens disposed within a particular adjacent row of tokens, or whether an abnormal operation condition has occurred (e.g., low rotation speed but high power input could indicate that the roller 1104 is stuck with debris and thus a cleaning cycle needs to be triggered in an attempt to dislodge the debris, and conversely a high rotation speed despite low power input could indicate that the roller 1104 is simply spinning because frictional engagement with the token is not being maintained properly. Load data is indicative of loads subjected on the components used and can be used for determining excessive wear, debris being jammed, mostly uses voltage and amperage calculations. For example, 0.06 A at 12 V, may be indicative of a normal operating condition. If it loads 0.25 A, likely something jamming, or less than 0.06 A, something in the transmission has failed. The motors may be configured to have more torque than necessary for rolling to ensure that something jams, it can overpower the jam short of mechanical failure (e.g., attempting rolling in different directions can be utilized to attempt to clear the jam).

In some embodiments, circuit board 1106 is operated in conjunction with tube counting sensors for fine-tuned analysis of load values and an improved determination of abnormal operation conditions. For example, if the circuit board 1106 is operated in conjunction with tube counting sensors that are either disposed within the central housing 1102 or an adjacent module (e.g., if the modules are spaced such that there is a tube counting module, followed by a roller module, followed by a tube counting module, and so forth), the load values can be increasingly accurately tied to an expected load based on a number and/or known size of tokens disposed with the aperture.

Figure 12:
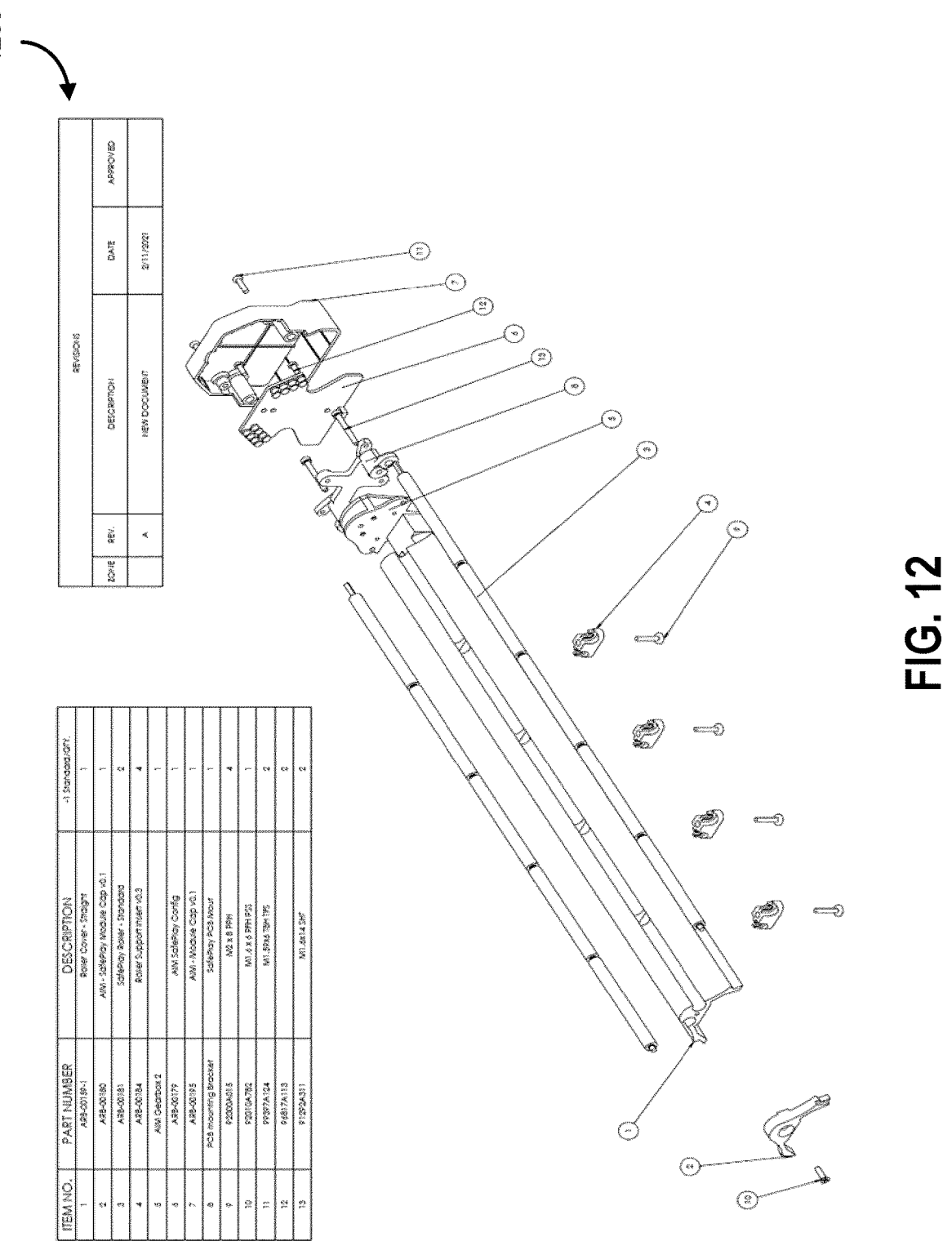
FIG. 12 is an exploded view of the modular roller insert, according to some embodiments.

FIG. 12 is an exploded view of the modular roller insert 1200, according to some embodiments. In FIG. 12, example component types are also illustrated in a table showing example types of components that can be utilized for practical implementation. The components listed are shown as examples and variations are possible.

Figure 13:
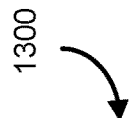
FIG. 13 is a side view of a roller showing an example D-cut axle, according to some embodiments. Other power transfer profiles are possible, and D-cut is shown as an example.
Figure 13:
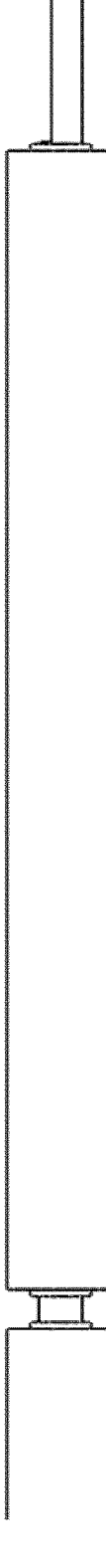
Figure 13:
Figure 14:
FIG. 14 is a perspective view of a roller support, according to some embodiments.
Figure 14:
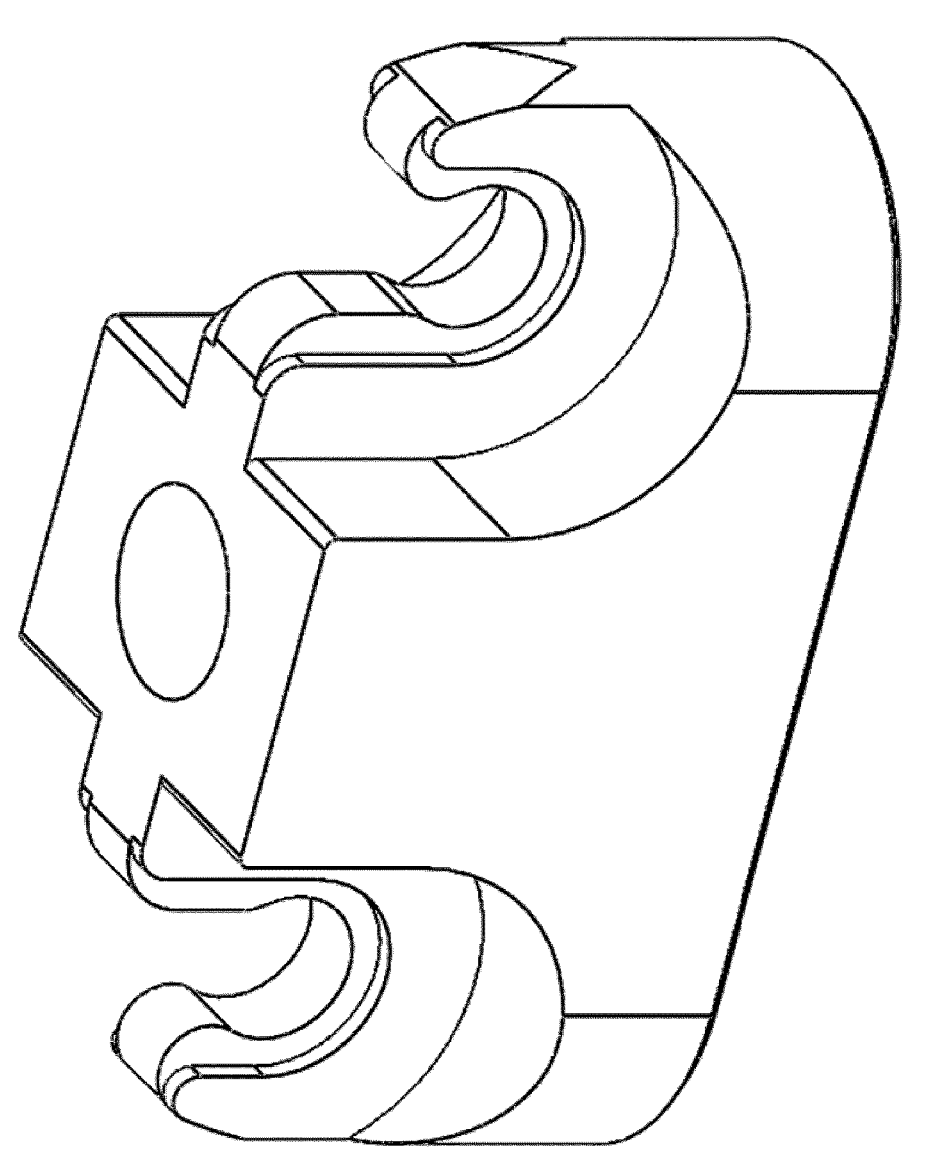

FIG. 13 is a side view 1300 of a roller showing an example D-cut axle, according to some embodiments. D-cuts allow for easy interfacing with a geartrain, and spacers can be provided to prevent additional friction from roller to roller supports. FIG. 14 is a perspective view 1400 of a roller support, according to some embodiments. The roller support is adapted to prevent axle from excess bending under chips, and helps restricts axial translation of rollers and clips onto axle, holding it in position. The roller support may be manufactured with a self lubricating plastic, such as Teflon or nylon, and composite materials may also be considered.

Figure 15:
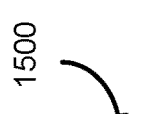
FIG. 15 is a perspective view of a first variation of a geartrain assembly, according to some embodiments.
Figure 15:
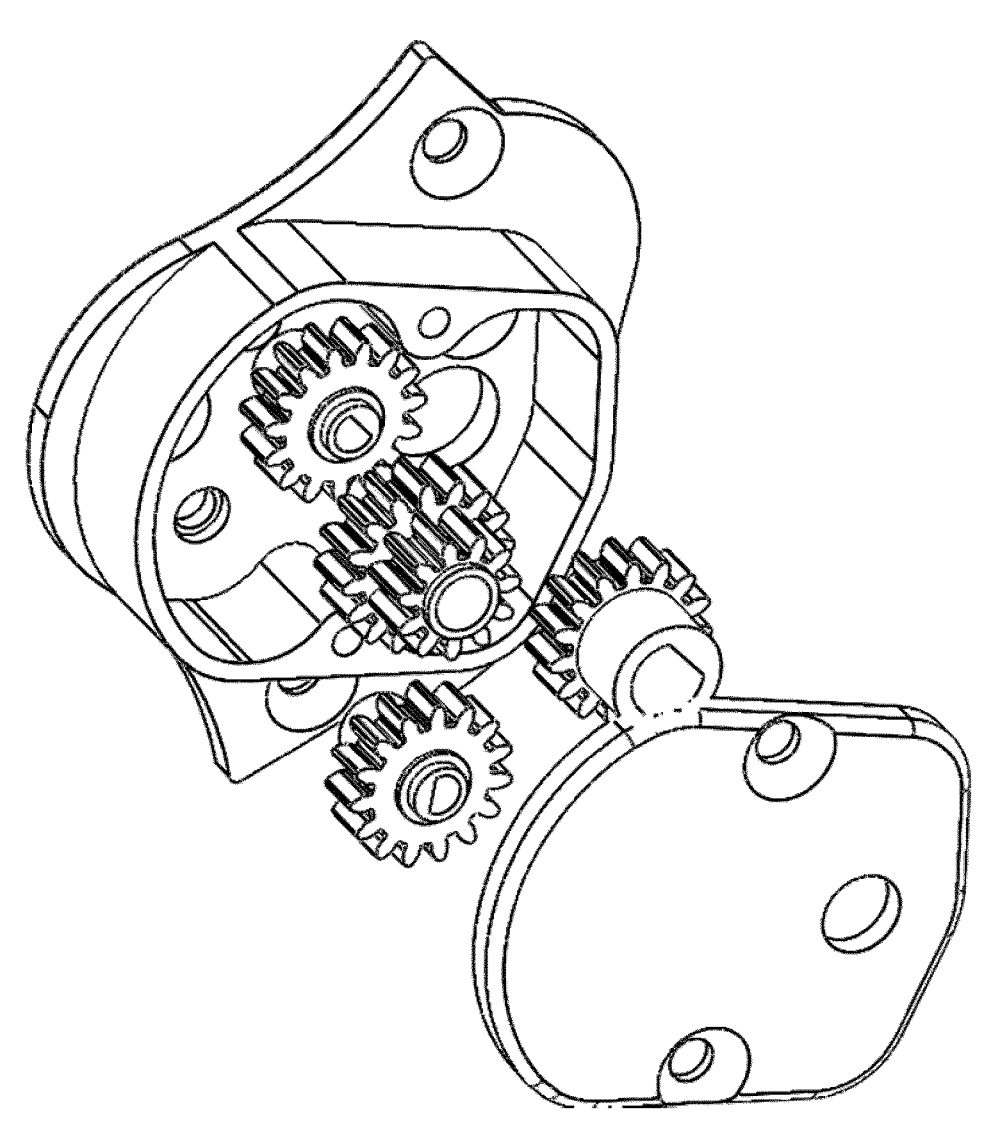
Figure 16:
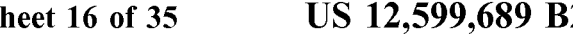
FIG. 16 is a perspective view of a second variation of a geartrain assembly, according to some embodiments.
Figure 17:
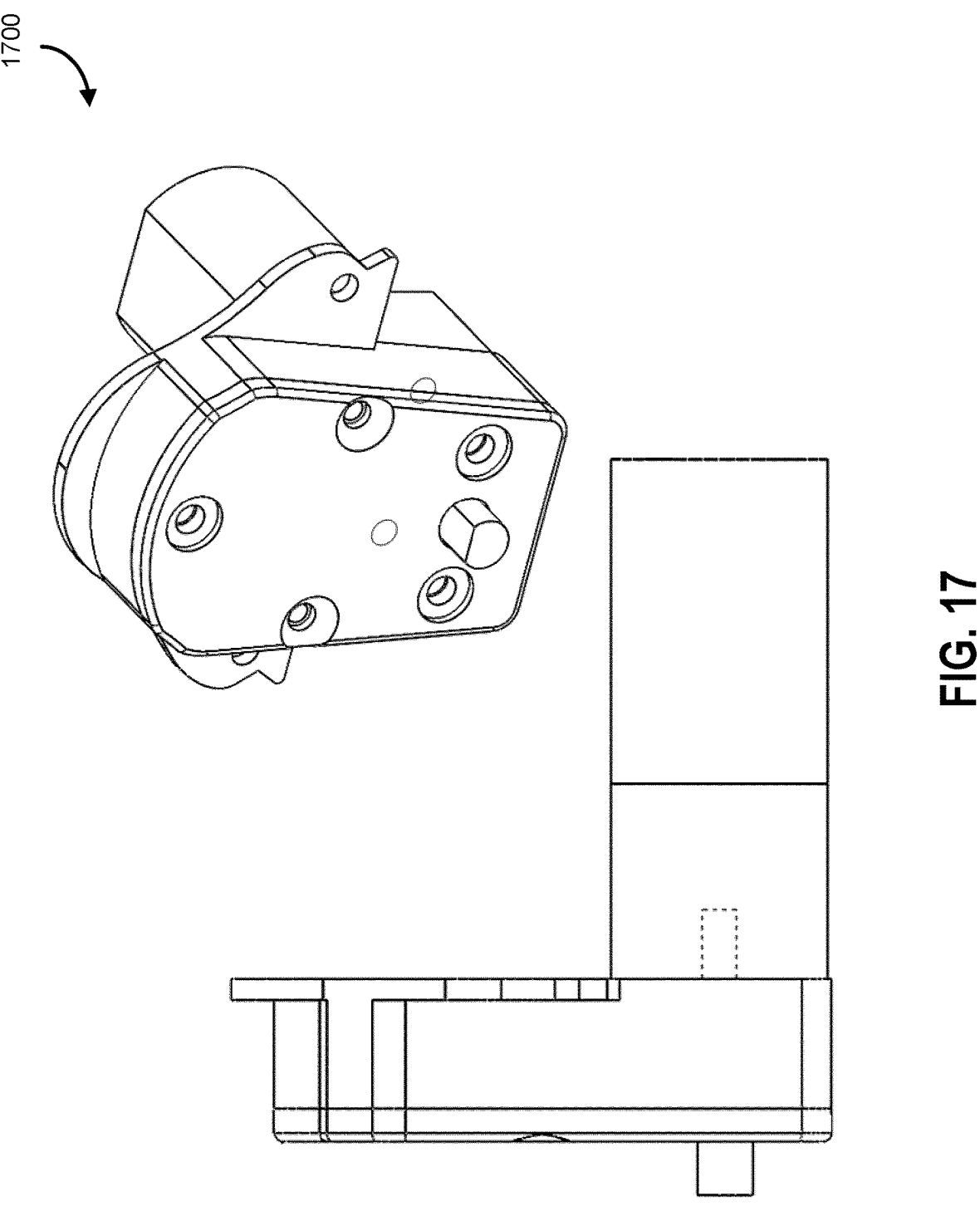
FIG. 17 is an perspective view of an assembled geartrain assembly, according to some embodiments.

FIG. 15 is a perspective view 1500 of a first variation of a geartrain assembly, according to some embodiments. FIG. 16 is a perspective view 1600 of a second variation of a geartrain assembly, according to some embodiments. In this updated version of the geartrain, the components are easier to assemble and maintenance is easier as there is more space for replacing motors, greasing buffers, and more space for electronics storage. FIG. 17 is an perspective view 1700 of an assembled geartrain assembly, according to some embodiments, along with a side view.

Figure 18:
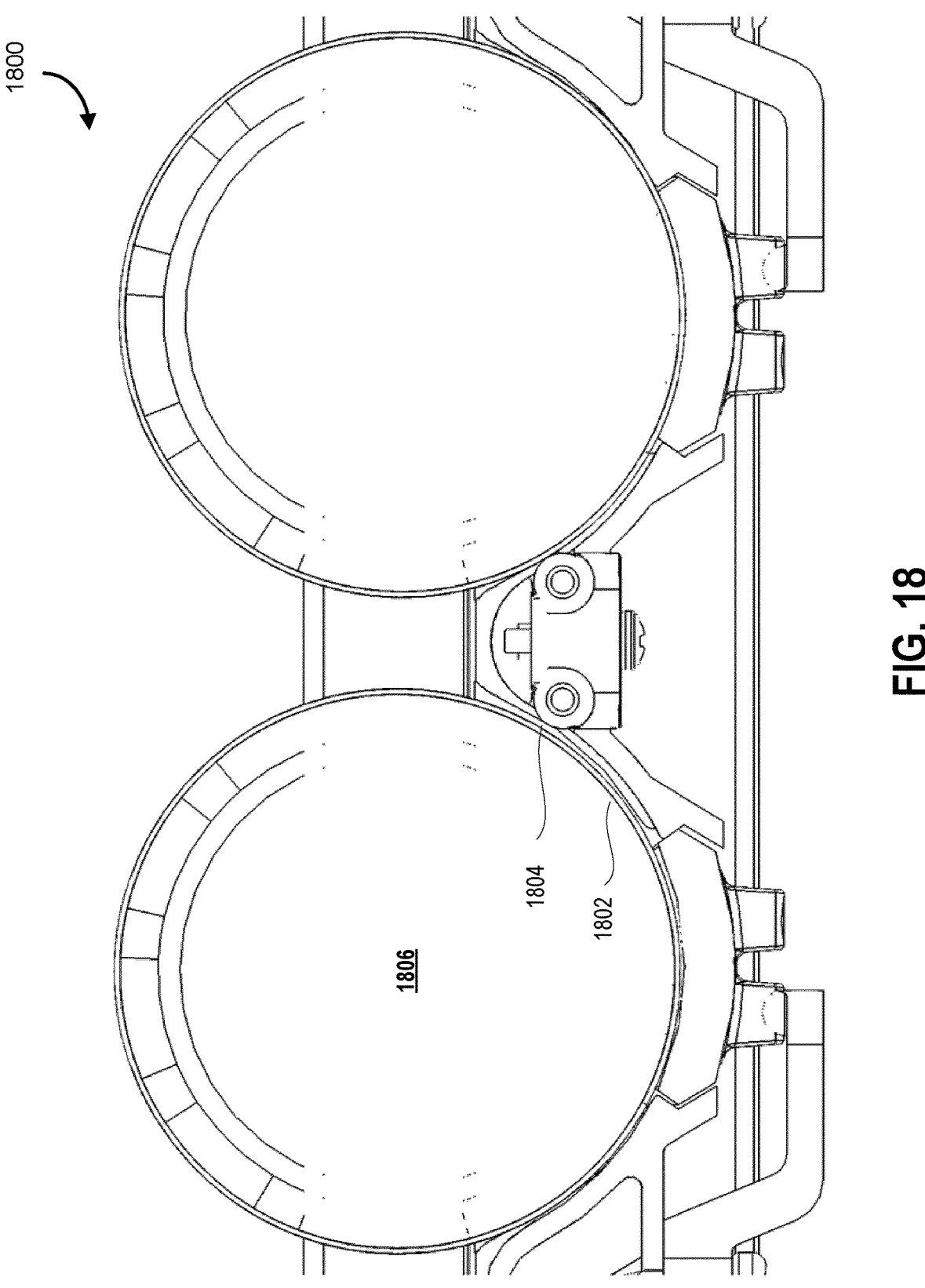
FIG. 18 is a cross-sectional view of one or more apertures holding cylindrical gaming tokens in parallel rows where a smaller chip diameter cylindrical gaming token is disposed within an aperture and the smaller chip diameter cylindrical gaming token rests or bottoms out on the aperture, according to some embodiments.

FIG. 18 is a cross-sectional view 1800 of one or more apertures holding cylindrical gaming tokens in parallel rows where a smaller chip diameter cylindrical gaming token is disposed within an aperture and the smaller chip diameter cylindrical gaming token rests or bottoms out on the aperture. In FIG. 18, a problematic condition is shown as the token 1806 where the token module units sit lower, resulting in the gap between the roller and the tokens 1804, and instead of resting on the roller, the token 1806 instead sits or rests on the bottom of the aperture tube at 1802, and there is a gap 1804 between the roller and the token 1806. Accordingly, when the roller rotates, there is no frictional engagement and the token 1806 does not rotate, and thus token 1806 is not properly sterilized during a sterilization cycle. This problem can occur, for example, when the token 1806 is smaller than the size of token the aperture was originally adapted to receive. This could occur with under-sized tokens, for example.

Figure 19:
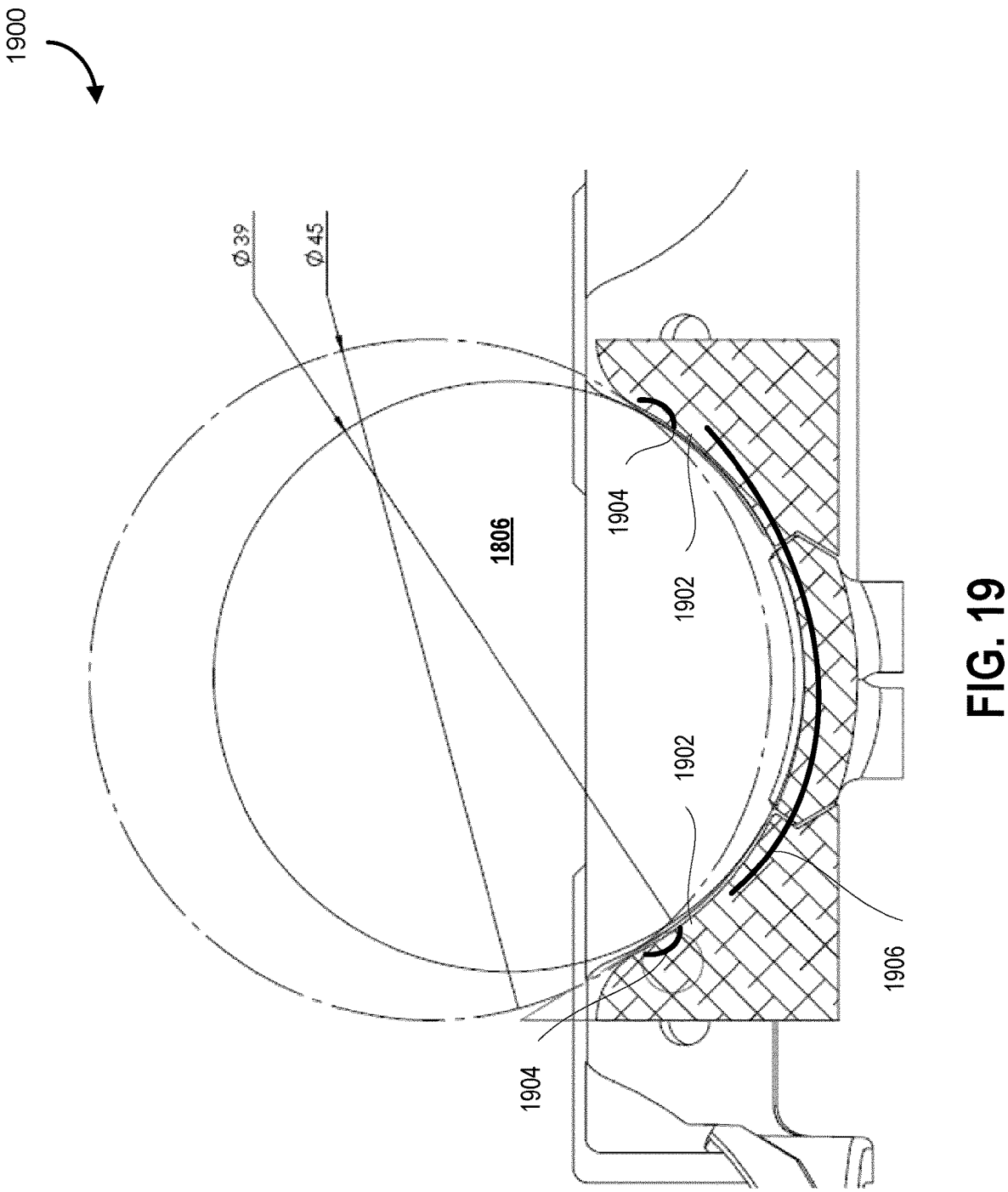
FIG. 19 is a cross-sectional view of an example aperture adapted to engage with a diversity of gaming token chip sizes, according to some embodiments. A number of token sizes are shown in this example.

FIG. 19 is a cross-sectional view 1900 of an example elliptical aperture adapted to engage with a diversity of gaming token chip sizes, according to some embodiments. In FIG. 19, the aperture and/or the sidewalls of the modular roller devices are shaped such that there is the depression upon which the token 1806 rests upon is no longer a circular depression, but rather, an elliptical depression 1902 which is either slightly longer than it is tall, or slightly taller than it is long. By utilizing an elliptical portion, the token 1806 no longer rests directly on a bottom of the aperture, and the contact point of the token 1806 is more likely to rest directly on a roller such that the roller can engage in a good frictional engagement with token 1806 for rotating the token 1806 for a sterilization cycle.

For a larger token, the contact points are only at the two thick lines shown at 1904, and for a smaller token, the contact points are all along a bottom shown in the thick line of 1906. The elliptical portion can be implemented using, in one embodiment, arced depressions that track a portion of an ellipse, either where a>b or b>a in $$\frac{x^2}{a^2} + \frac{y^2}{t^2} - 1.$$

Either a or b does not have to be substantially greater than one another; a slight change to provide for an elliptical depression may be enough to clear manufacturing tolerance deviations and/or to provide for an improved geometric profile to adapt to a diversity of token diameters.

Figure 20:
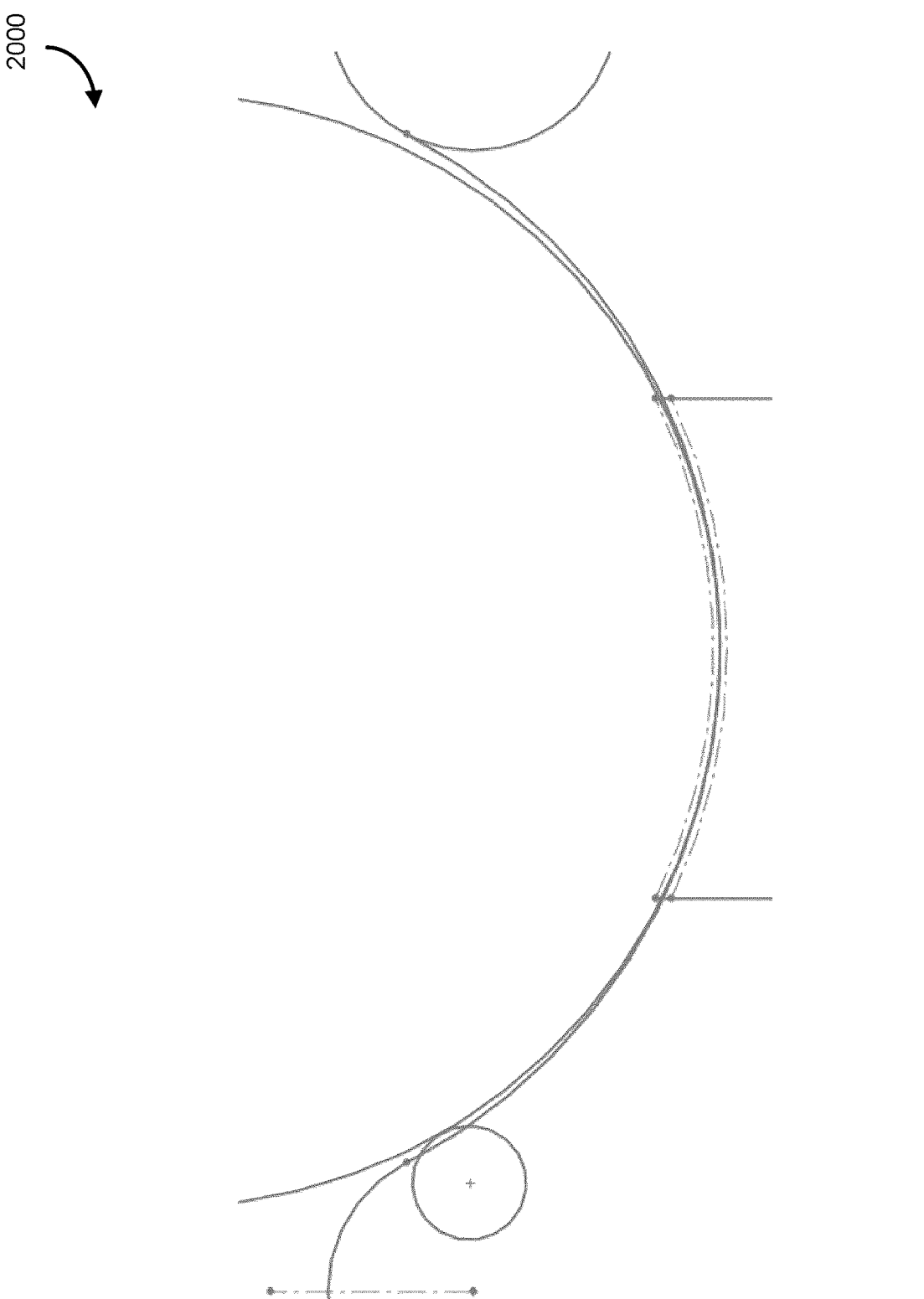
FIG. 20 is a cross-sectional view showing a simple small chip with offset error, shown by dotted lines, representing relative position offset and potential interference positions, according to some embodiments.

FIG. 20 is a cross-sectional view 2000 showing a simple small chip with offset error, shown by dotted lines, representing relative position offset and potential interference positions, according to some embodiments. Similar to differing sizes of the tokens, additional offset module errors can occur as a result of manufacturing inconsistencies, which are exacerbated when it is important to utilize lower cost manufacturing approaches for manufacturing the tubes for holding the tokens. Utilizing an elliptical depression 1902 also aids in reducing the impact of manufacturing inconsistencies as the elliptical depression 1902 causes the token to rest at a higher point that is more likely in frictional engagement with the roller. An example, a ruler may be resting on table with two pencils, those are 'high points' or contact points, the offset error that occurs is a bigger pen stuck between the desired pencils, allowing the ruler to only contact one of the intended points.

Figure 21:
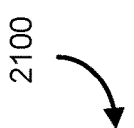
FIG. 21 is a cross-sectional view showing a simple large chip with offset error, shown by dotted lines, representing relative position offset and potential interference positions, according to some embodiments. In this example, a collision is shown between two large tokens.
Figure 21:
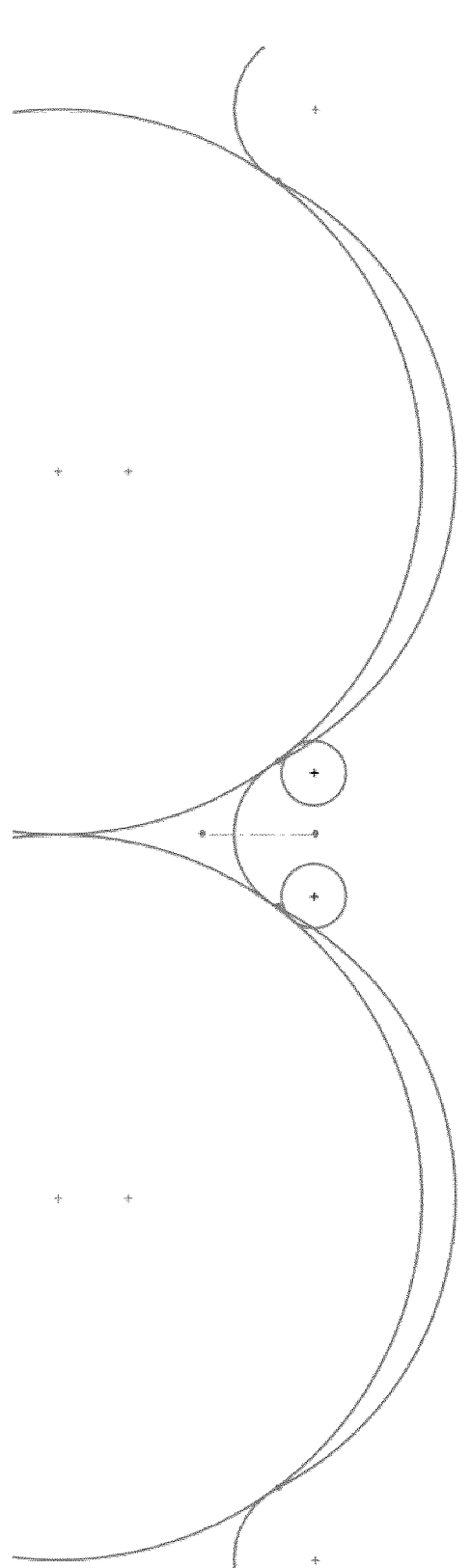

FIG. 21 is a cross-sectional view 2100 showing a simple large chip with offset error, shown by dotted lines, representing relative position offset and potential interference positions, according to some embodiments. Offset errors can also occur as a result of inconsistencies in roller positioning from the insertable module itself. In the drawing of FIG. 21, a further challenge can arise when the tokens themselves are so large that they overlap with one another and come into contact with another due to not being seated within into the bottoms of the apertures, or the tokens may also rest on non-roller portions of the insertable modules, reducing an ability of the rollers to rotate the tokens.

Figure 22:
FIG. 22 is a cross-sectional view showing another simple large chip with offset error, shown by dotted lines, representing relative position offset and potential interference positions, according to some embodiments.
Figure 22:
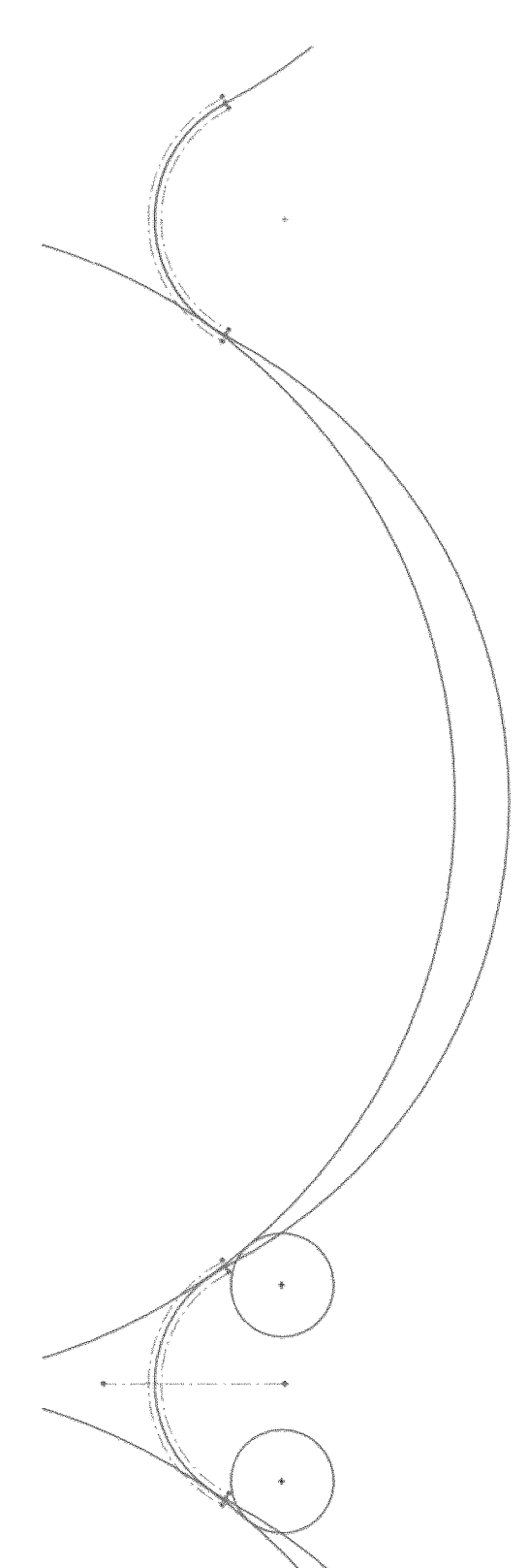

FIG. 22 is a cross-sectional view 2200 showing another simple large chip with offset error, shown by dotted lines, representing relative position offset and potential interference positions, according to some embodiments. In FIG. 22, the dotted lines represent an arbitrary offset of the modular units when installed. When they sit high or low, they create high/low points of contact with the chips, and the adjacent modular unit. In this case, the roller. The chip may sit high/low on the roller and may also have a third contact point right above the roller causing the token to have a 'imbalance' of contact points, making rotation intermittent or not at all. A token may physically sit above the roller due to the offset errors, when otherwise could normally operate, and various design updates can help accommodate these issues as well.

Figure 23:
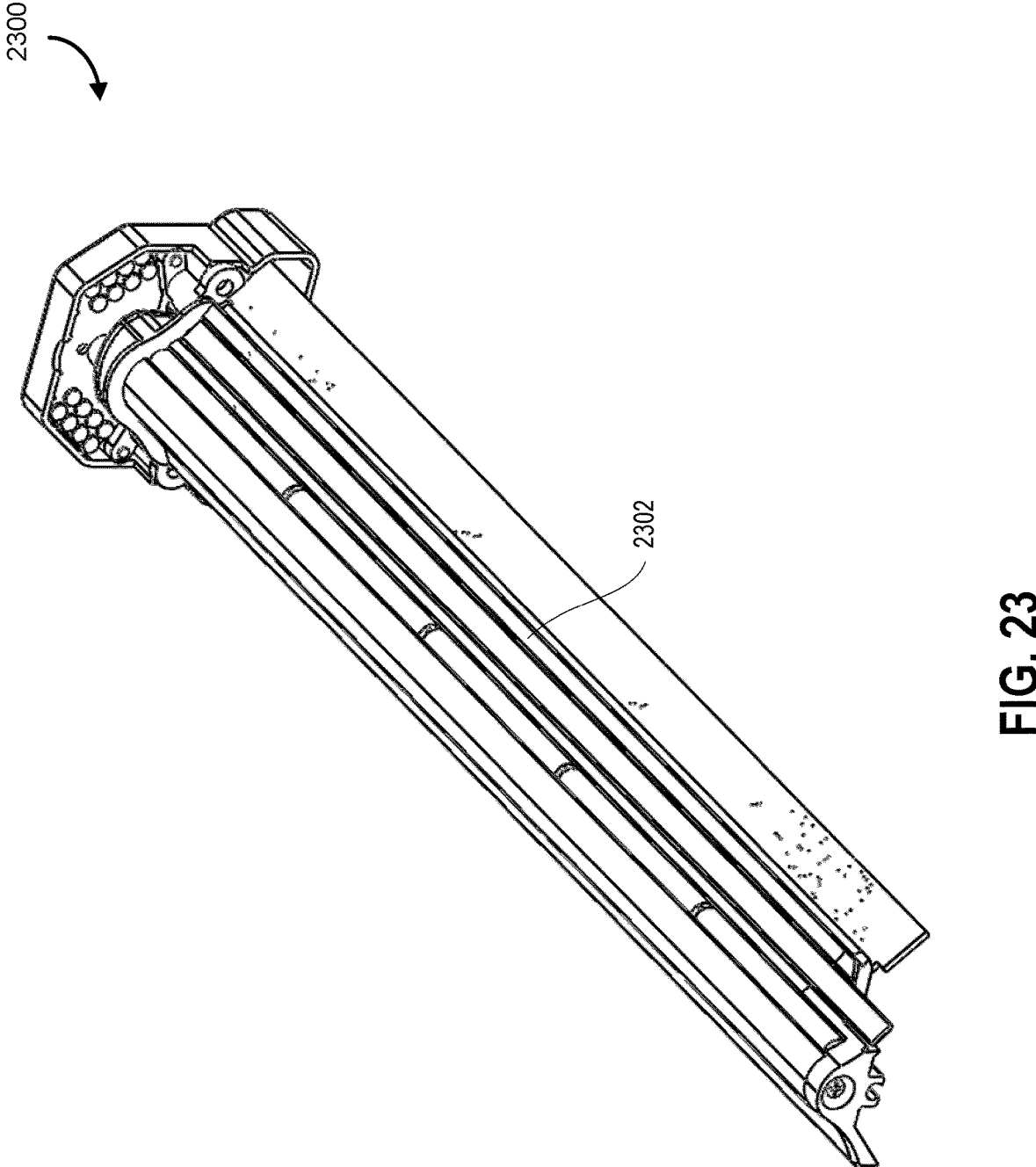
FIG. 23 is a perspective view of an example roller module, according to some embodiments.

FIG. 23 is an perspective view 2300 of an example roller module, according to some embodiments. This 'variant' or combination is generally used for occupying the first and last slots of the modular system, to allow both functions within the first and last tubes (roller and tubecount, as an example. It can be expanded to simplify manufacturing or parts lists, and also allow for additional features in the neighboring module slots/positions. The module shown in 2300 is a dual purpose module that can fit into various slots. In this improved roller module, the roller module has both rollers and optical sensors adapted for tracking the number or position of tokens residing within the aperture (e.g., a "tubecount"). The tubecount can be represented, for example, as a chip count, tray/tube occupancy value/utilization, etc. The optical sensors 2302, for example, could shine an incident light on the tokens and identify, by utilizing a suitable corresponding photoreceptor, which positions reflect the incident light indicating that the position or slot has been filed with a token. An improved tray may include that described in U.S. application Ser. No. 16/622, 676, filed 13 Jun. 2018, entitled "SYSTEMS, METHODS AND DEVICES FOR MONITORING GAMING TABLES", incorporated herein by reference.

The optical sensors 2302 can include photoreceptor/photoemitter pairs, which can correspond each to specific locations in an aperture in which a token may reside. When the photoemitter generates an emission, the received signal (or lack thereof) by the photoreceptor can indicate the presence or absence of a token in that particular slot. The sensed data sets can then be utilized to establish, for each position, whether a token is there or not, whether it has been interacted with recently (e.g., comparing against tracked memory), which can then be utilized to establish a tube-Count variable indicative of how full a particular aperture is. In some embodiments, the accuracy of the tubeCount variable can also be verified or validated through a short activation of the rollers to perturb the tokens and then conducting a re-measurement to see if the tubeCount has changed.

In some embodiments, the optical sensors 2302 are further configured or augmented with additional sensors providing photoreceptors for tracking levels of ultraviolet emissions. The readings from the optical sensors 2302 can then be utilized as a mechanism for providing a feedback loop for tracking the amount (e.g., dose) of sterilizing emissions a particular section or region of the gaming equipment tray has received.

The "tubecount" data can then be utilized by the controller circuit of the roller module in more accurately determining whether load conditions are normal or abnormal based on an expected loading determined accurately from the number of tokens in the aperture. For example, a tube loaded with 50/100 tokens may have an expected loading that is proportional to the 50 tokens, and if the controller circuit determines that the perceived loading is that of 150 tokens, an abnormal condition (e.g., roller is stuck, causing maximum load) is possible. In an example, a standard tube may have slots for 65 tokens. The expected loading value can be assigned a constant depending on an expected chip size or difficulty of rolling and then multiplied by the number of chips. If the roller is experiencing a greater or reduced load beyond a threshold range (e.g., +/−10%, 5%, 3%, 1%), an abnormality flag may be raised by the controller, which can either cause a downstream repair request or an attempted cleaning cycle to be automatically initiated (e.g., the roller is configured to roll forwards and backwards in an attempt to automatically dislodge debris).

Figure 24:
FIG. 24 is an enlarged perspective view of the example roller module, according to some embodiments.
Figure 24:
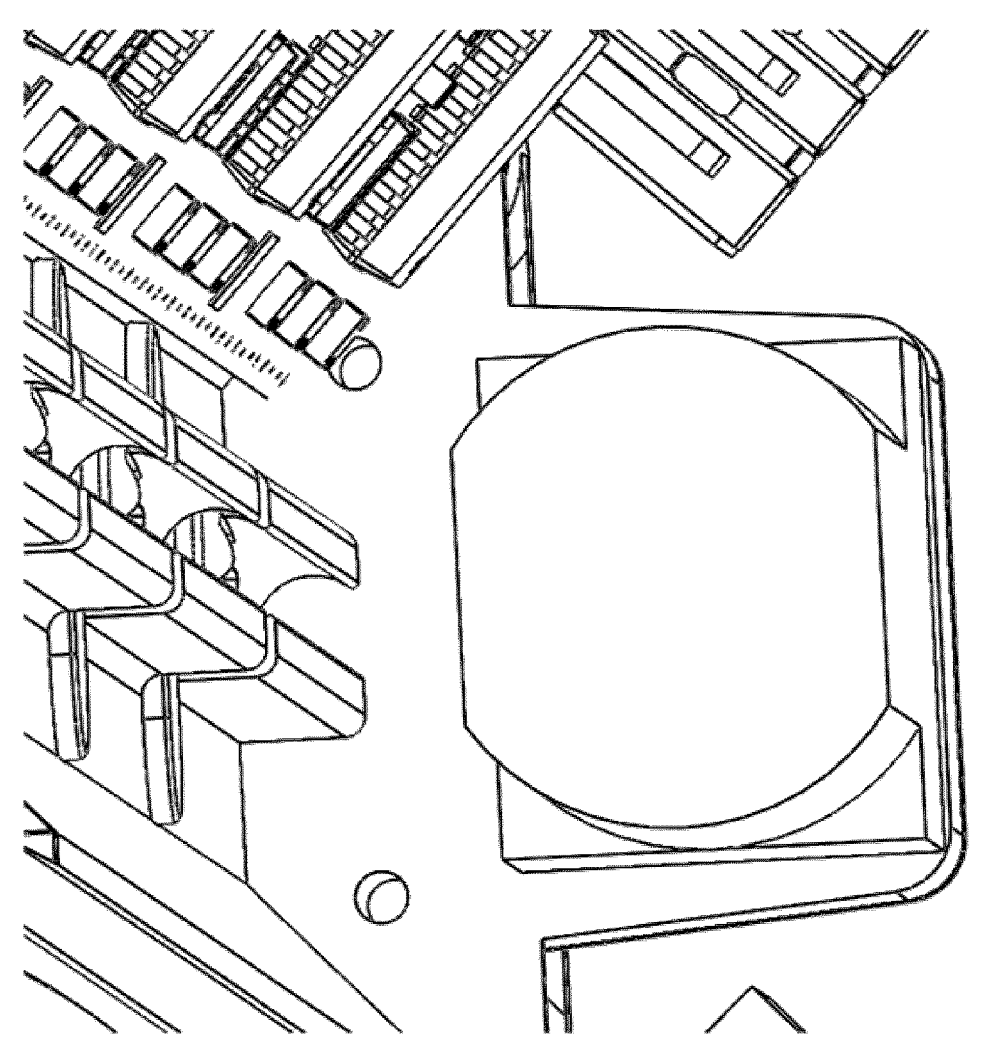
Figure 25:
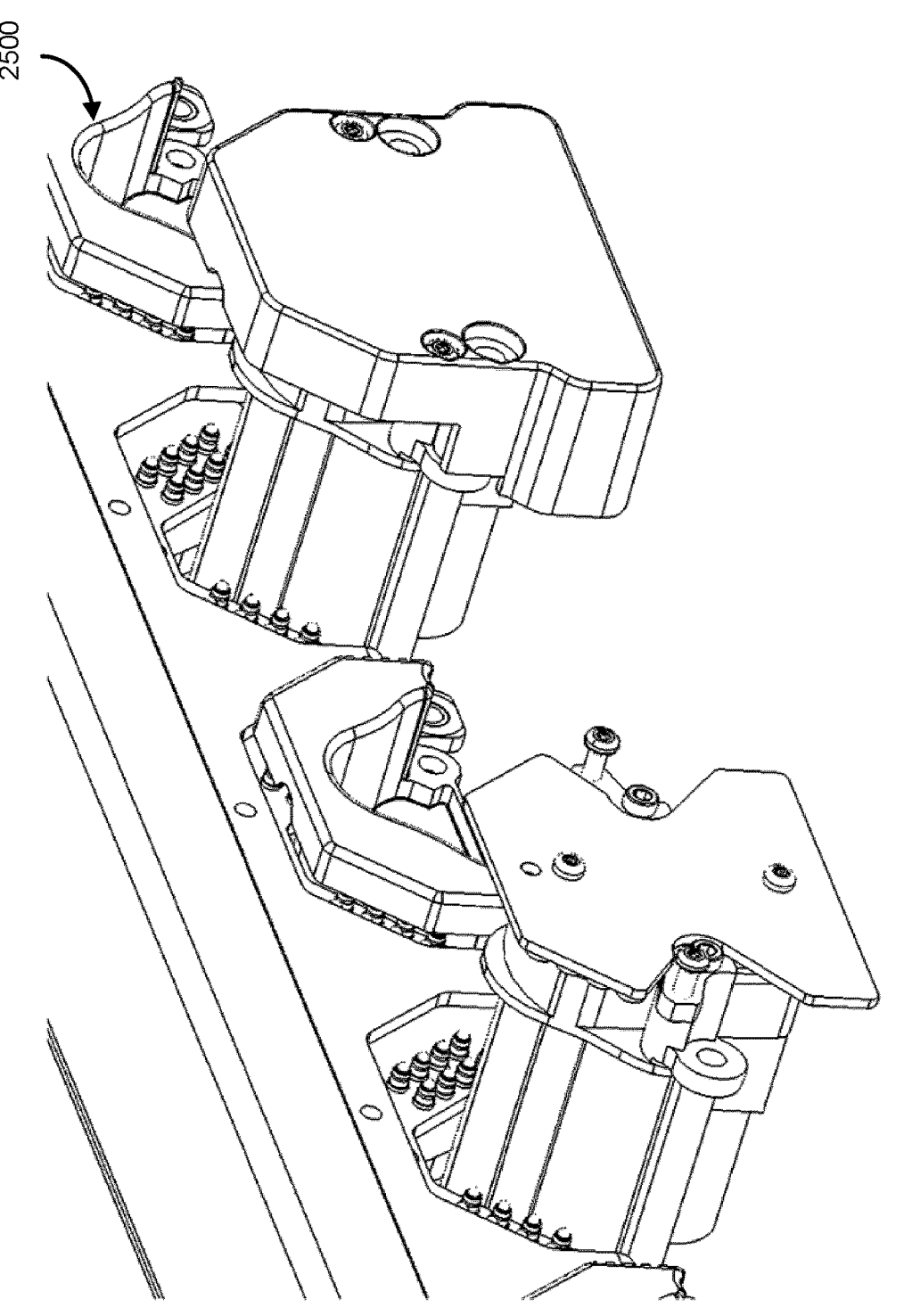
FIG. 25 is an enlarged perspective view of the example roller module showing interface printed circuit boards and module control boards, according to some embodiments.
Figure 26:
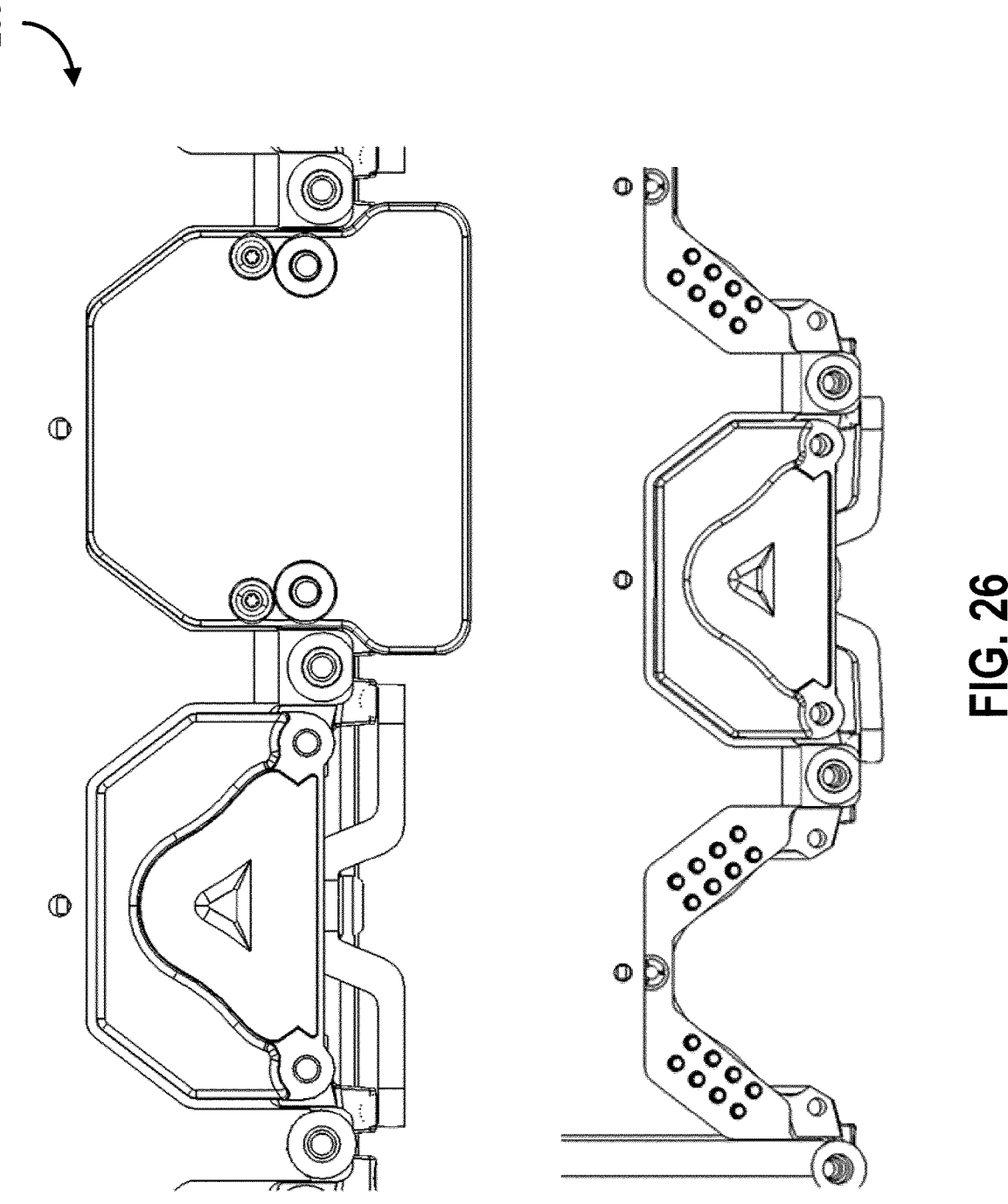
FIG. 26 is a rear view showing a gaming token receiver tray having modules and also another version having receptacles for receiving roller modules, according to some embodiments.

FIG. 24 is an enlarged perspective view 2400 of the example roller module, according to some embodiments. An improved clearance is shown between the motor and onboard electronics. The additional clearance afforded by the updated geartrain allows for common parts for future variant upgrades, by allowing space for support of mechanical features, computation (stacked electronics), wires, tubing, links, cams, levers, or other embodiments not mentioned. FIG. 25 is an enlarged perspective view 2500 of the example roller module showing interface printed circuit boards and module control boards, according to some embodiments. During installation, the roller module unit can be inserted into a corresponding slot/receptacle. FIG. 26 is a rear view 2600 showing a gaming token receiver tray having receptacles for receiving roller modules, according to some embodiments. Two modules are shown here, on the left, a blank module is shown, and on the right, an adjacent roller module is shown.

Figure 27:
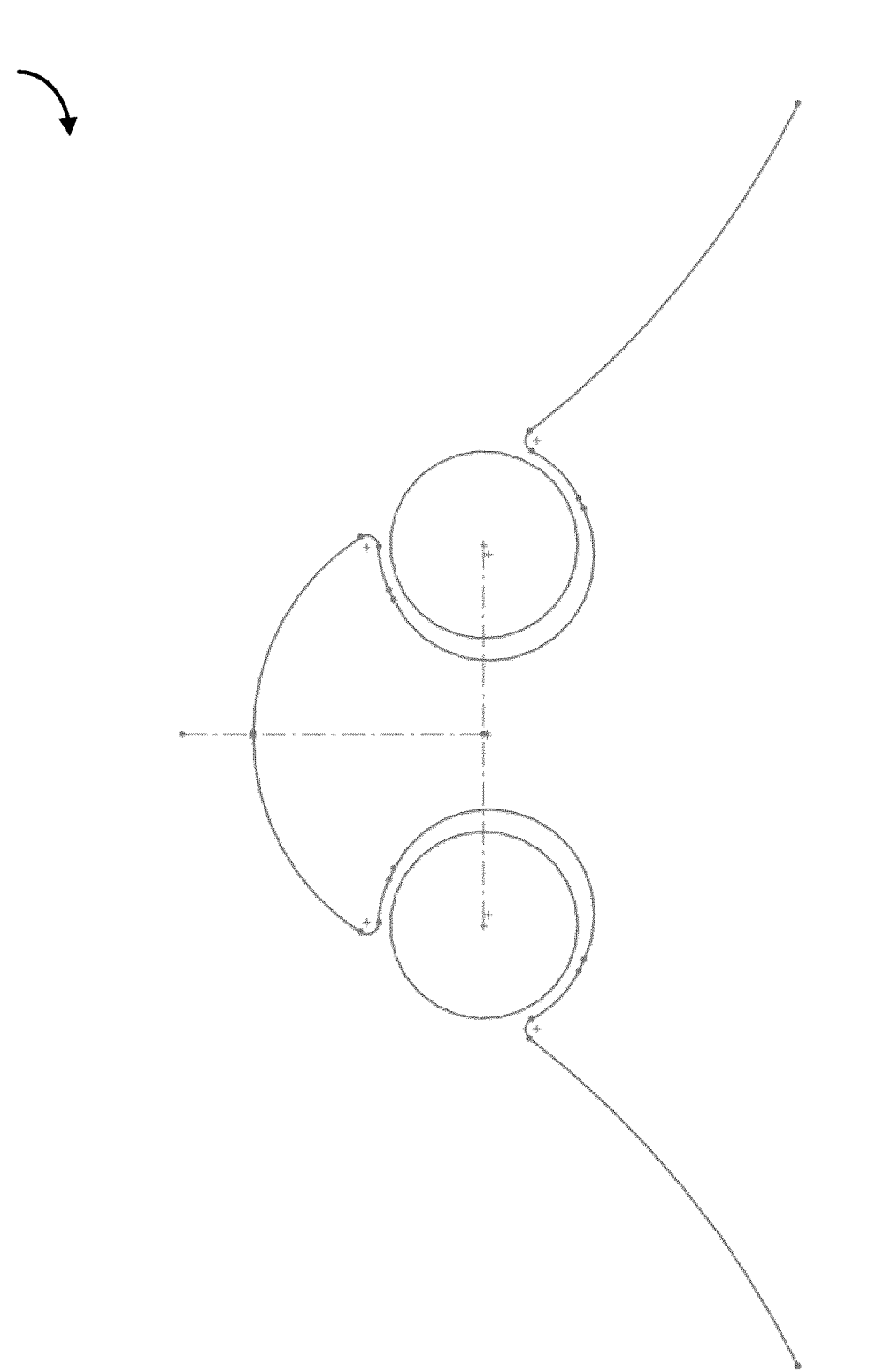
FIG. 27 is an example cross sectional view of rollers, according to some embodiments.

FIG. 27 is an example cross sectional view 2700 of rollers, according to some embodiments. A slot-like channel can be provided to allow for roller deflection without causing excessive internal contact. The position of rollers relative to the tube helps reduce risk of debris becoming lodged between the rollers and channel and allows the opportunity to automatically clear the debris. Excessive drag can trigger a 'clearing event' where the unit reverses direction to attempt to clear the rollers of debris, and close fitment helps prevent intentional jamming of axles due to minimal space available for insertion.

Figure 28:
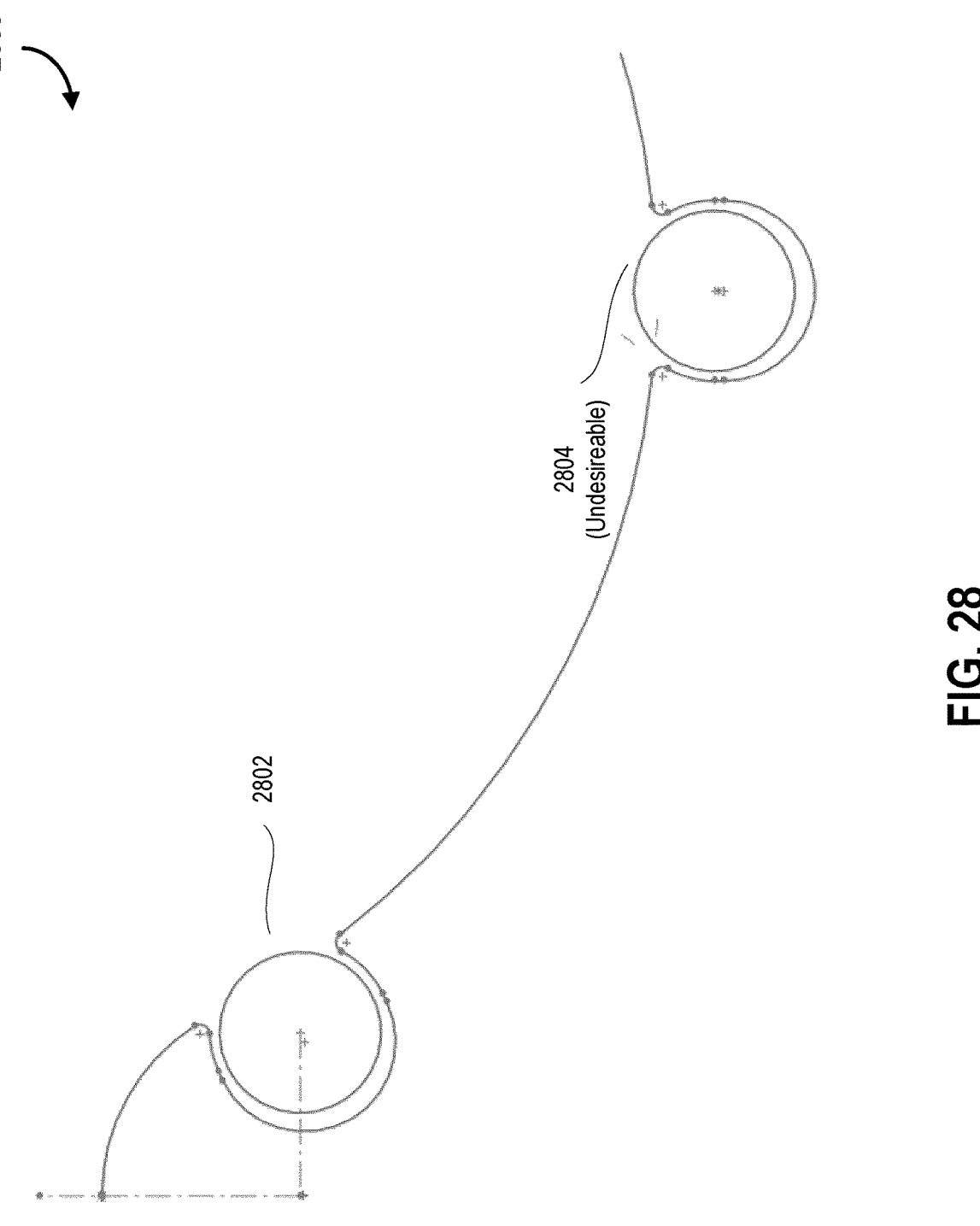
FIG. 28 shows potential positions for rollers, according to some embodiments. Rollers are preferentially positioned along a diagonal side of the rollers as opposed to the bottom of an aperture, according to some embodiments, or in a higher positioned location along the aperture interface profile for interacting and position gaming equipment and to effect intended actuation.

FIG. 28 shows potential positions 2800 for rollers, according to some embodiments. Rollers are preferentially positioned along a diagonal side 2802 of the rollers as opposed to the bottom 2804 of an aperture, according to some embodiments. In 2802, the rollers are in a suggested position as opposed to bottom center at 2804 (roller maybe positioned anywhere along tube, including in lid). Rollers are positioned to have an improved opportunity to effect their purpose (token roll in this case), and the desired placement helps deal with the variance of chip sizes likely to be encountered.

If positioned along the diagonal side 2802, rotation of the suggested position can roll clockwise or counter clockwise, to clear debris lodged in channel (direction depends on Left/Right side). In the scenario shown in 2804, debris in the lower section of the tube has no opportunity to be cleared (the debris may be stuck permanently) and no amount of direction changes can clear it short of maintenance. A lower position of rollers also does not work well for larger tokens (due to floating).

Figure 29:
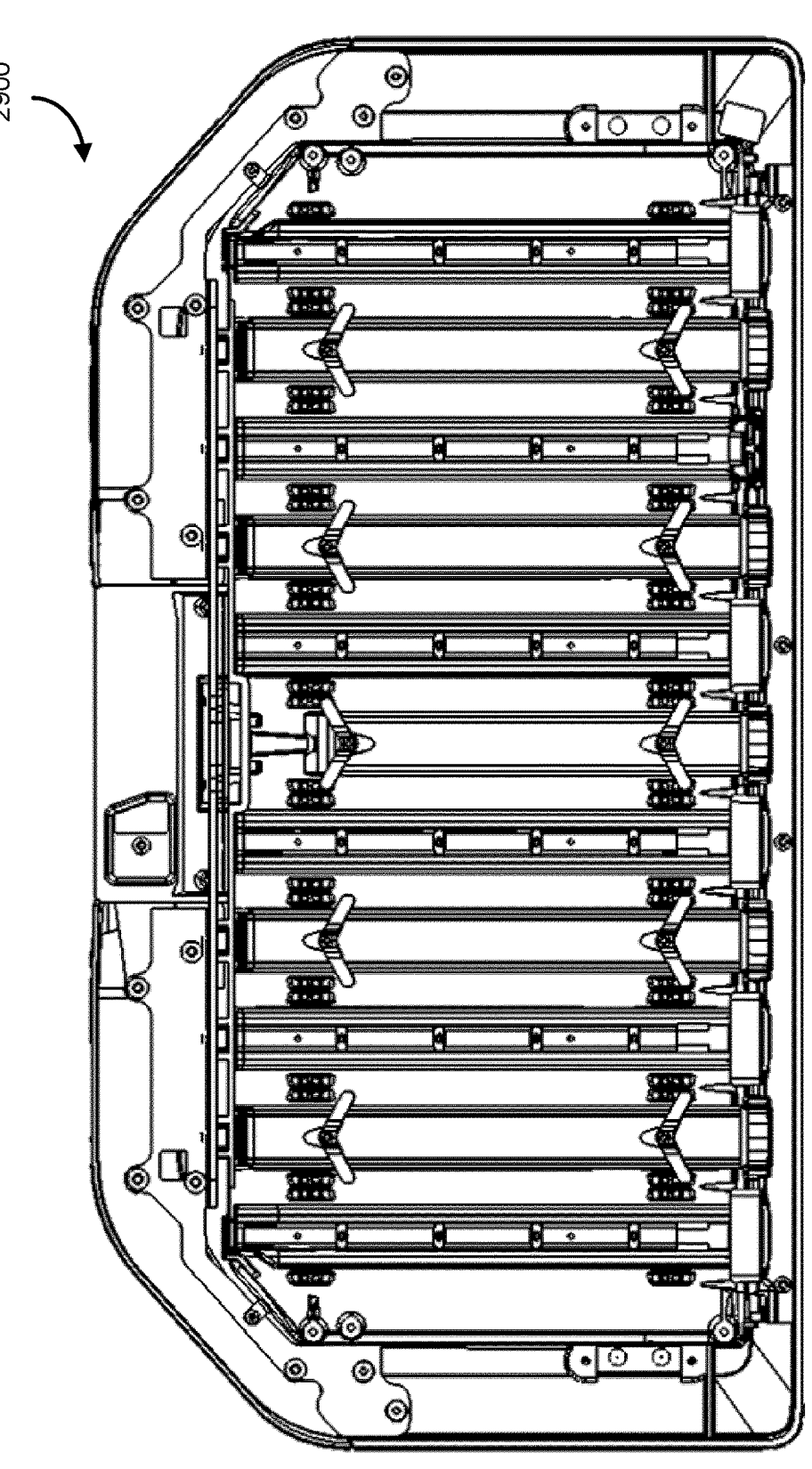
FIG. 29 is an example overview view of the gaming token tray having modular roller devices disposed therein, according to some embodiments.

FIG. 29 is an example overview view 2900 of the gaming token tray having modular roller devices disposed therein, according to some embodiments.

Figure 30:
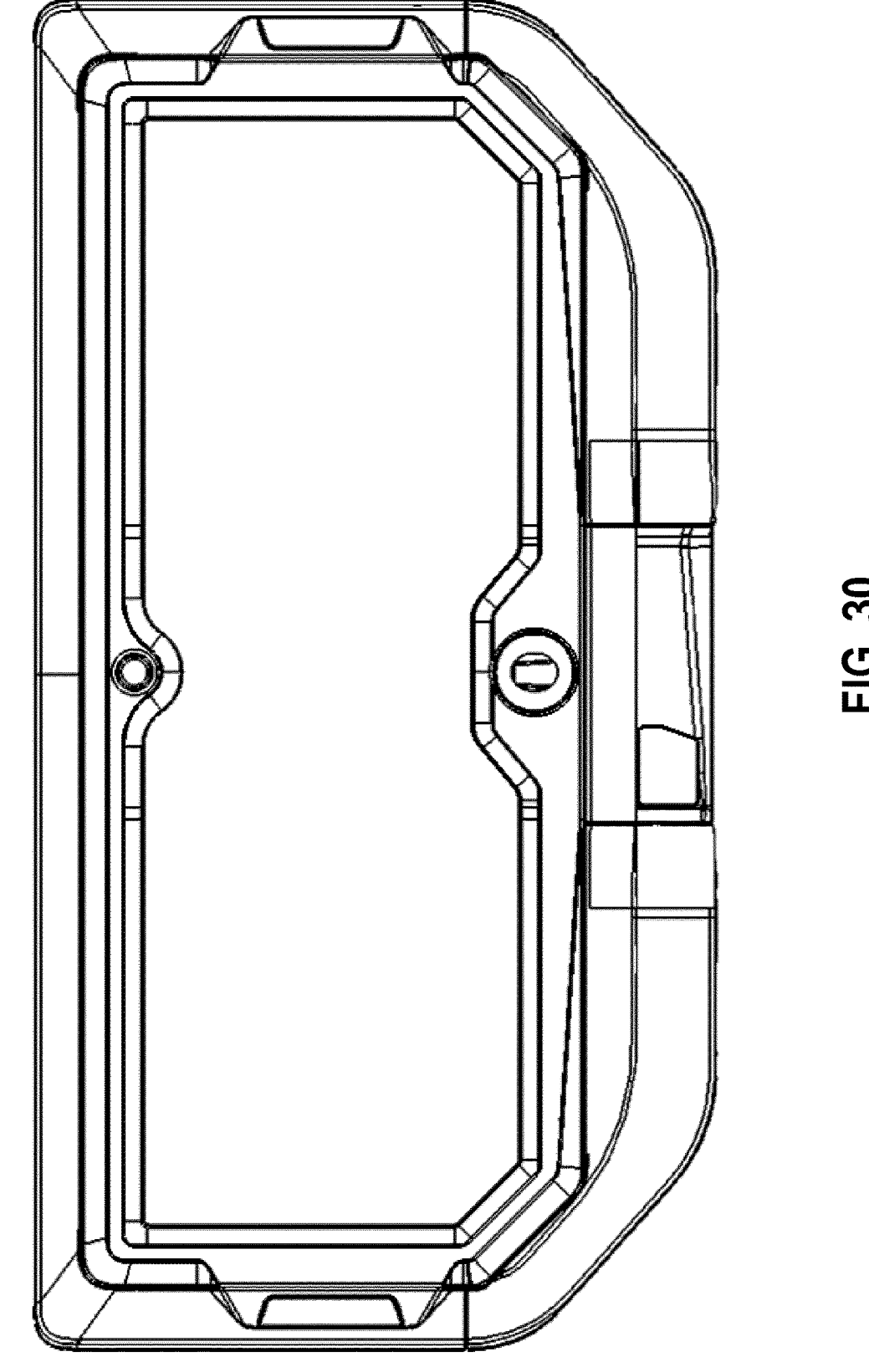
FIG. 30 is an example overview view of the gaming token tray lid housing, according to some embodiments.

FIG. 30 is an example top view 3000 of the gaming token tray lid housing, according to some embodiments. The gaming token tray lid housing can include coupled lights and/or buttons that can be used to show status of the sterilizing cycle or manually turn on the gaming token tray lid housing, respectively. For example, different colors, or patterns of light can be provided to indicate different status events in a cleaning cycle.

Figure 31:
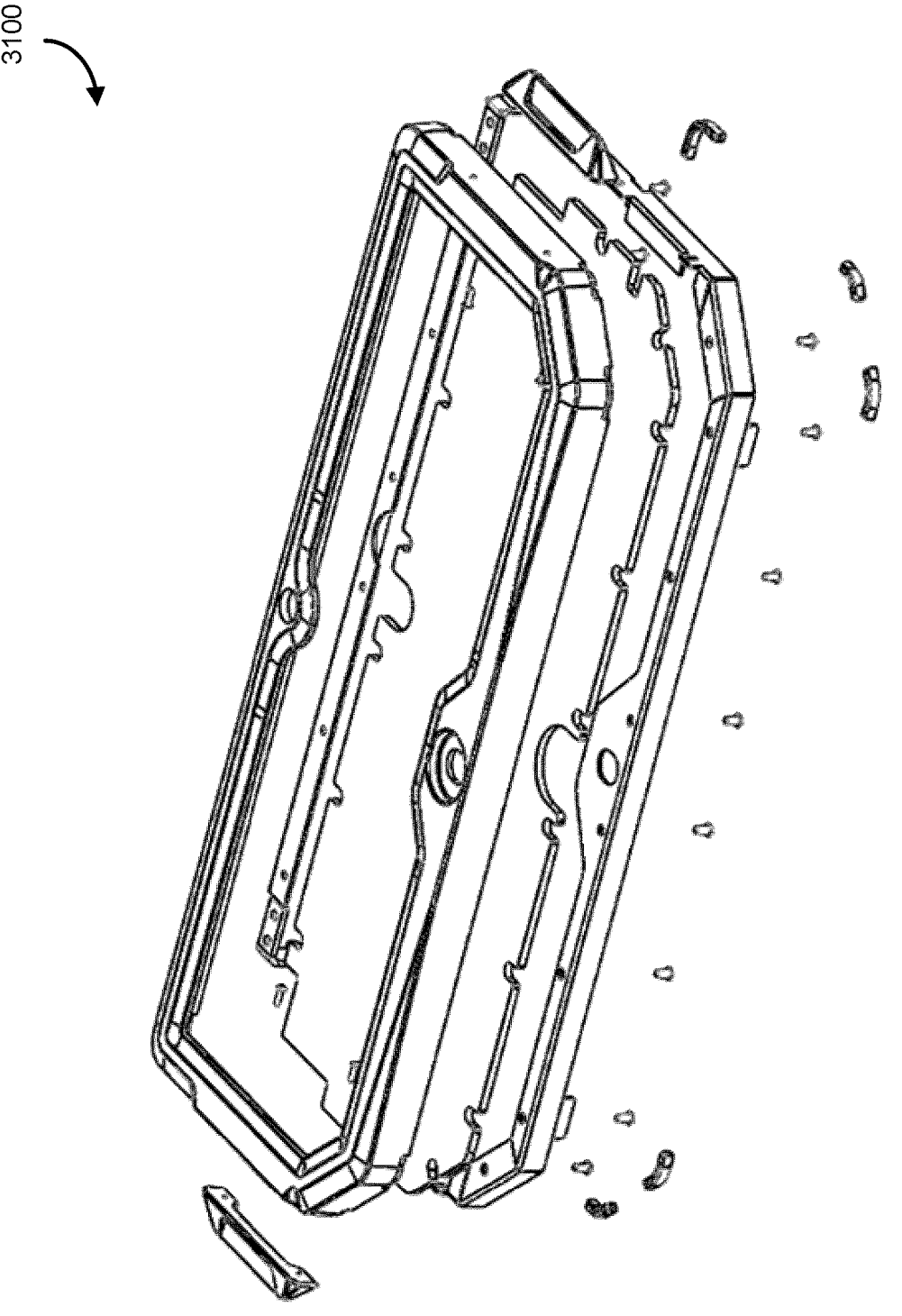
FIG. 31 is an example perspective view of the gaming token tray lid housing placed overtop of the gaming token tray, according to some embodiments.

FIG. 31 is an example perspective view 3100 of the gaming token tray lid housing placed overtop of the gaming token tray. In this example, there may be complementary mating points that together complete an electrical circuit such that power is transferred to the gaming token tray lid housing for powering the sterilizing light as well as indicating that the gaming token tray lid housing is correctly positioned overtop the gaming token tray.

Figure 32:
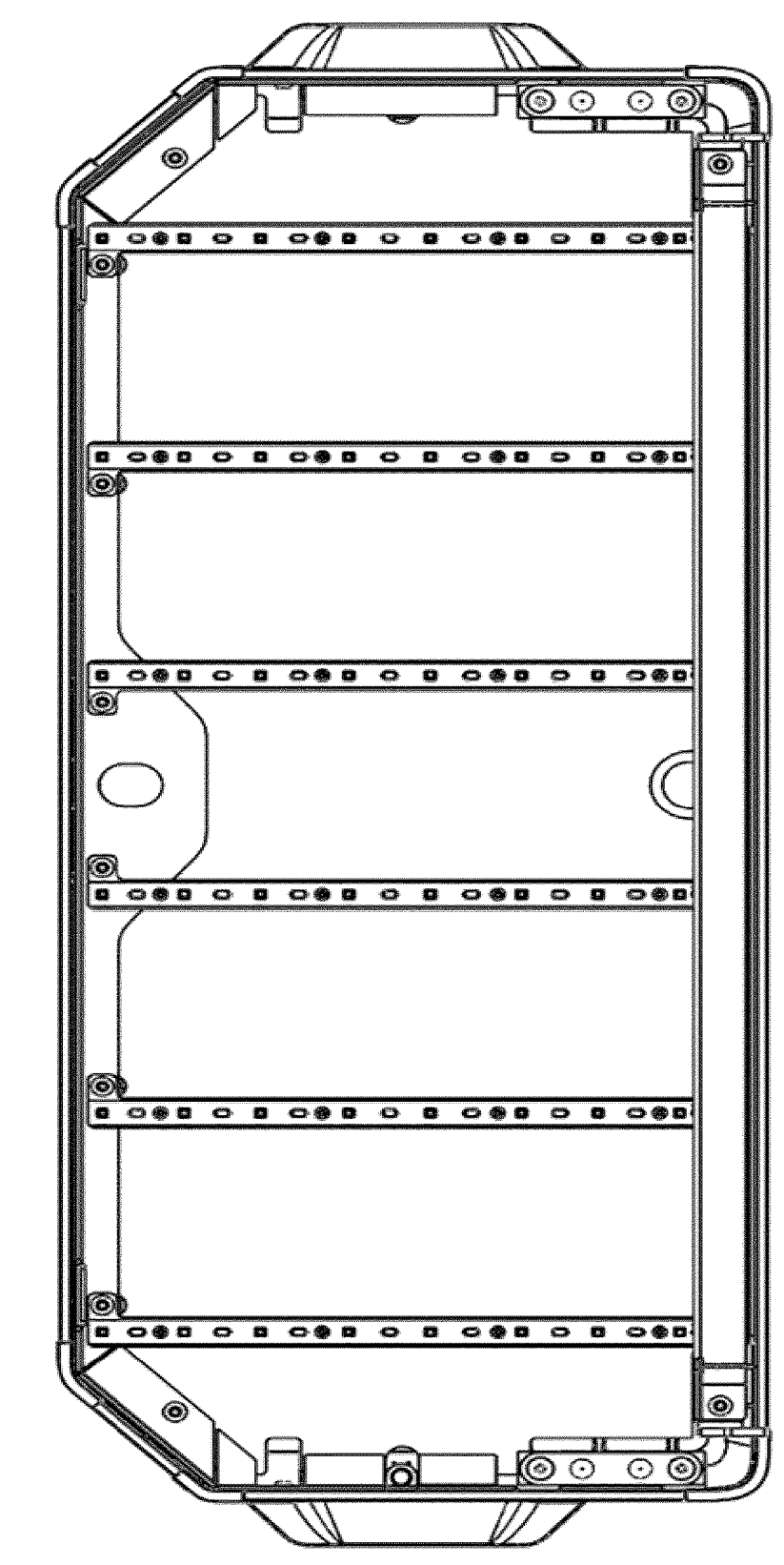
FIG. 32 is an example bottom view of the gaming token tray lid housing showing a plurality of sterilizing light emitting light sources, according to some embodiments.

FIG. 32 is an example bottom view 3200 of the gaming token tray lid housing showing a plurality of sterilizing light emitting light sources, according to some embodiments. In experimentation, sterilizing light emitting light sources were experimented with LED strips as well as UV-C bulbs, and it is important to note that UV-C light exposure could be dangerous to users and thus safe operation during only when a lid is properly seated on the complementary tray may need to be established using electrical circuits or sensors which only allow the lid to activate when there is no or reduced risk of UV-C light exposure on the users. A security window may be provided so that a user is able to safely observe that the emission is taking place.

Figure 33:
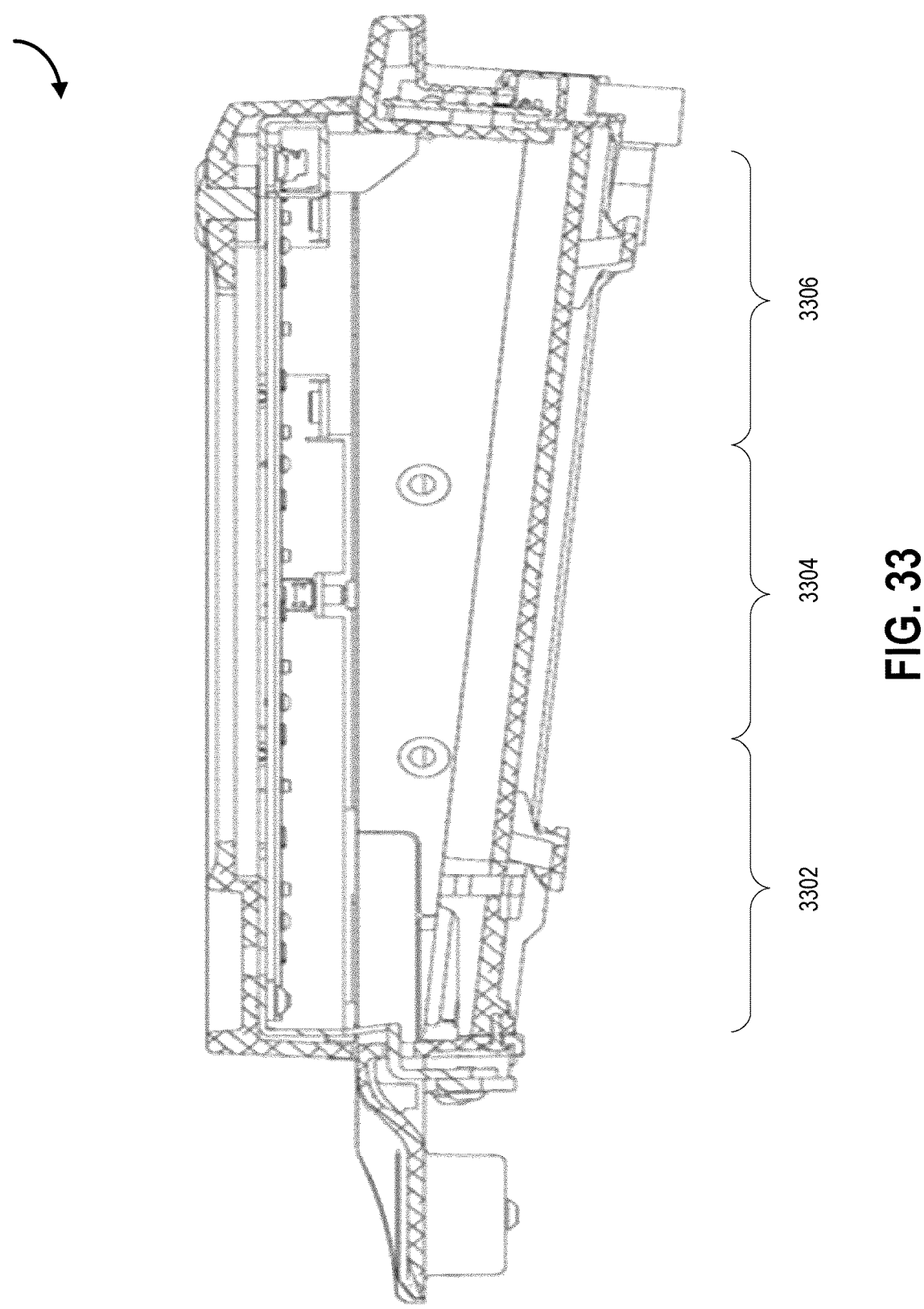
FIG. 33 is a side view of the gaming token tray, according to some embodiments.

FIG. 33 is a side view 3300 of the gaming token tray, according to some embodiments. In this view, the gaming token tray has a slope downwards, and the dealer would be positioned on the right side of this view. The dealer interacts with the tokens in a stack—tokens are inserted and removed from the left hand side of this view, in an example. As tokens are inserted and removed from the same side, this causes certain tokens and regions of tokens to have a higher level of "touch" and "action", and in some embodiments, sterilizing activities can be directed based on tracked amounts of touch and action, and the distribution thereof of such high touch/high volume tokens. Similarly, tokens nearest the dealer (e.g., on the right side of this image), may have less overall "touch", and in some situations, remain completely untouched from one sterilizing cycle to another as they are far down the stack (utilized only when, for example, a high denomination chip is being broken into smaller denominations and a large number of chips are required to be obtained from the stack. In another example, tokens are removed from a 'left to right' method, tokens added in a right to left method, and tokens can also be added as a group, and these movements can be tracked.

The controller circuit of the module may be configured to either have on-board sensors for tracking token/tube activity to track an accurate "tubecount", or may interoperate with another module specializing in counting token movement to determine the "tubecount". Accordingly, token removal/insertion activity can be determined and tracked on a simplified basis by establishing different zones, such as zones 3302, 3304, and 3306 shown in annotations. In some embodiments, the zones 3302, 3304, and 3306 are more complex and are broken down by tubes, or broken down both by tubes and regions within the tubes. For example, the controller may track usage based on proximity to dealer, and establish a semi circle that can be used to track a heat map (showing, for example dead center chips very unlikely to be used, while chips in corners (furthest from dealer), dealer dominate hand or closest to active player/s, may have increased utilization).

Because of the slope downwards, the duration of time required for sterilizing the tokens in each of the different zones increases based on how close they are to the dealer (because of the slope, the distance to the emitter changes). As those tokens are relatively undisturbed, in some embodiments, if the controller circuit and sensors interoperate to determine that only a particular zone of tokens or region has been interacted with since the last cycle, a shorter duration of time can be utilized to sterilize the tokens.

The duration of time is driven by the 'dosage rate' of the emitter, for example, if only the first zone of chips was handled, then due to the proximity to the emitter, the duration can be reduced while still achieving set cleaning level. As each zone that needs to be cleaned, the duration must be set for the duration required to clean that zone. For example, zone 1=1 min, Zone=3 min, Zone 3=5 min. For a Session A, Zone 1 is only used, duration=1 min. Session B=Zone 3, duration=5 min. etc.

The positioning of the tokens as detected by optical sensors 2302 and movement of tokens in the tube over a period of time can also be utilized to modify the operation of the sterilization cycle by the controller. The controller circuit may, in on-board memory, designate memory regions to tracking specific zones of movement within each aperture, the zones designed by geographical area, and in some embodiments, each zone being associated with a sterilizing distance value (important where the gaming equipment tray itself has a slope).

In the example where the roller module either has access to or has onboard optical sensors 2302 for tracking which tokens have been interacted with over a period of time, the controller may maintain in data structures in memory which zones have been interacted with, creating, over a period of time, a heat map of interactions. In some embodiments, the memory values may simply by a Boolean value for a grid of positions (e.g., x, y) where once contact has been made, the value is switched to TRUE. In another embodiment, the memory values are instead a counter in an array representing the grid of positions, such that every contact increments the counter. The memory values may be reset every time a successful sterilization cycle is completed.

If each zone is assigned a sterilizing duration (e.g., due to the distance from the emission source), the sterilization duration can be set as the maximum duration of all zones that have been triggered by the interactions, thereby minimizing the overall duration (e.g., if only tokens from Zone A were interacted with and Zone A requires the least sterilization time due to the proximity to the emitter, then the sterilization duration can be set to a lower time). In the example with the counter being incremented, the duration for a particular zone may be modified by the amount of interaction. For example, if a counter indicates a 15, and 10 is a minimum threshold to trigger sterilization for Zone A, then Zone A would have to be sterilized. In another example, the minimum required duration for a particular Zone may be determined based on the amount of interaction (e.g., areas with high amounts of interaction may presumably carry more virus, mold, bacteria, and thus a longer clean would be required). Similarly, in this example, the overall sterilization time may be the highest number associated with all triggered Zones (e.g., Zone A=30 seconds, Zone B=2 minutes, Zone C=5 minutes, set durationSterilization=max(ZoneA, ZoneB, ZoneC) such that the duration sterilization=5 minutes in this example.

In the example table below, example contact Count and contact Boolean values are shown with example modified sterilization durations controlled by the controller circuit. The objective of utilizing a zone-based approach is that it provides a mechanism for reducing the overall sterilization duration (and thus the amount of time a tray cannot be used) while still maintaining coverage at least over tokens that have been contacted with or interacted with. This is particularly important when the sterilization occurs at the dealer table itself.

module housing 3506 from inadvertent exposure to UV-C damage from the emitter, an additional reflector 3508 is provided. The reflector 3508 is adapted to be complementary to the module to reduce inadvertent exposure by the gaming equipment container, and the module inserts (e.g., to avoid color washing off of plastics and finishes). The reflector 3508 aids in ensuring that the light is more focused and reduce duration of sterilization.

The emitter can, for example, emit 15 mW/cm^2, and have different radiation amounts depending on distance. For example, the UV dose can vary from 10 mJ/cm^2 to 3000 mJ/cm^2 over a duration of time based on a distance, as due to dispersion, the amount of emission on a particular region may drop off quickly due to distance from the emitter.

| Zone A (10 mm away from emitter, section furthest from dealer) Duration = 30 seconds | Zone B (15 mm away from emitter, section furthest from dealer) Duration = 2 minutes | Zone C (20 mm away from emitter, section furthest from dealer) Duration = 5 minutes | Sterilization Duration |
|---|---|---|---|
| Contact = TRUE, contactCount = 15 | Contact = TRUE, contactCount = 5 | Contact = FALSE | 2 minutes |
| Contact = TRUE, contactCount = 21 | Contact = FALSE | Contact = TRUE, contactCount = 15 | 5 minutes |
| Contact = TRUE, contactCount = 26 | Contact = TRUE, contactCount = 1 (not greater than threshold of 5) | Contact = FALSE | 30 seconds + 26 × 1 seconds = 56 seconds |

In another embodiment, the controller circuit may also track a wear level of the roller assembly based on an expected number of rotations adjusted for different encountered load levels. Accordingly, the accurate load information over time reported from the dual purpose module can also be utilized to more accurately gauge the wear level for indicating, for example, to a central table management software or interface computer that a particular roller module unit needs to be replaced as it has reached its maximum mileage given the specific loading conditions to which it was exposed to. The wear level can be tracked, for example, using a locally stored counter variable on local storage that has weighted increments based on a load level, among others, or it can be more accurately tracked on the central table management software for coordinated replacements. Wear levels can be tracked on the onboard memory of the controller circuit of each module and interrogated (e.g., polled periodically, or an interrupt signal can be raised) in communication with a backend table management platform such that modules can be flagged as worn down and ready for replacement.

As the modules are typically physical consumables with a known lifespan, the ability for modular insertion and replacement and tracking of wear is an important consideration for smooth operation in a fast-moving gaming facility. In an embodiment, the wear levels tracked in memory can be a counter variable that tracks a number of actuations, and the wear counter can further be modified (e.g., weighted) using measured load values from operation at the gaming facility or a number of sterilization cycles.

Longevity tests can be performed and module swapping schedules can be established alongside maintenance schedules.

Figure 35:
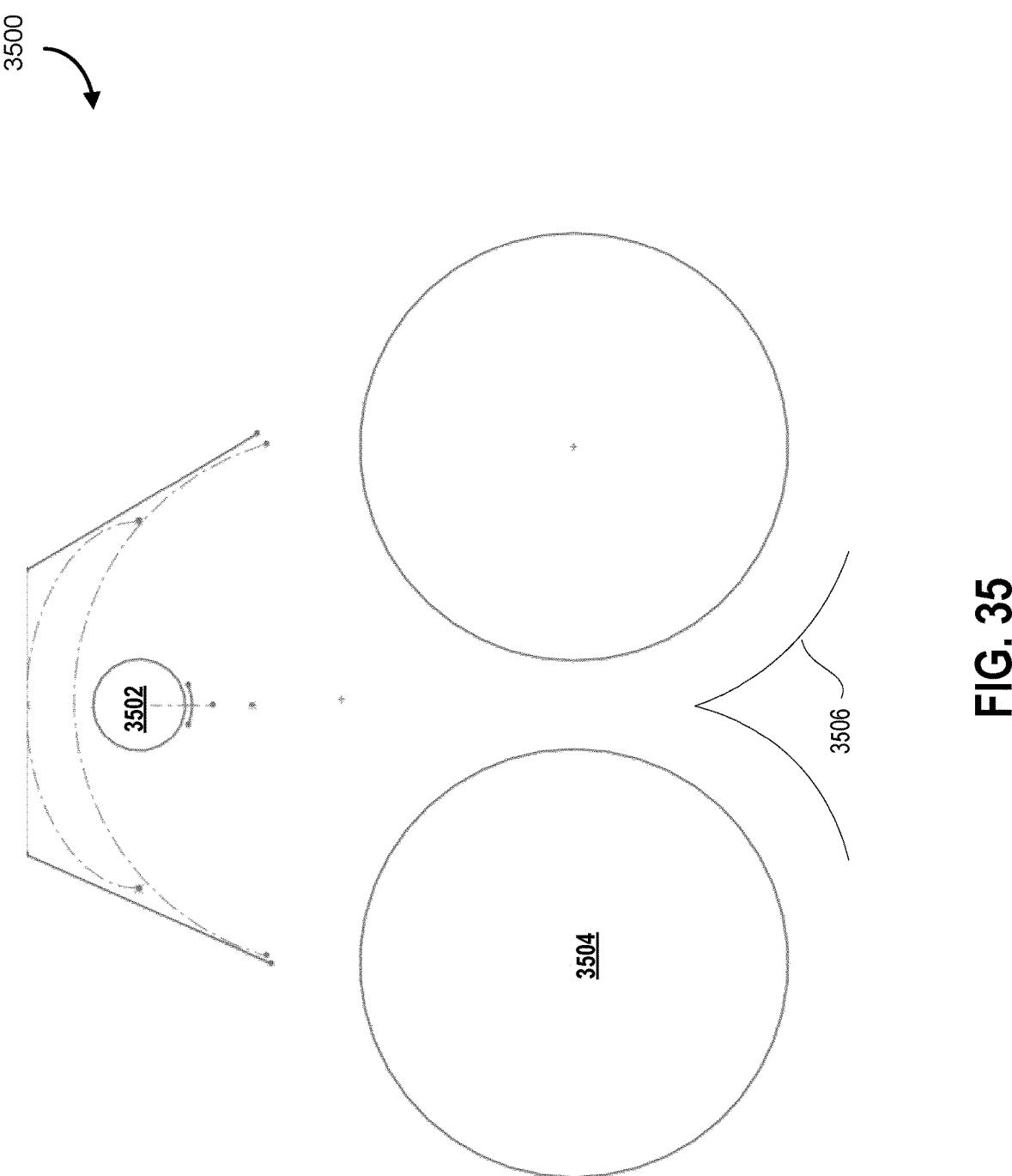
FIG. 35 is a cross-sectional drawing directed to an example reflector arrangement for protecting the module housings from UV-C exposure, according to some embodiments

FIG. 35 is a cross-sectional drawing 3500 directed to an example reflector arrangement for protecting the module housings from UV-C exposure, according to some embodiments. In FIG. 35, the emitter 3502 is positioned in the lid housing above the tokens 3504. In order to protect the Applicants conducted testing to assess dosage of an example module, and experimented using a source having the following characteristics 8×1 w UV LED, @ 43 v (wired in series, 90% power) of varying height, min. 1 mm proximity to 20 mm (determined based on 39 mm diameter token to be sterilized). In this example, it was found that a minimum dose rate of 5 mJ/cm^2/min for a duration of 5 min would be needed to reach the sterilization objective, and variations were further considered for testing with different proximity, and LED density.

Applicants tracked sterilization emission amounts using dosimeters in five minute intervals, and noted the amounts for specific distances. 6 experiments were conducted, to track various amounts of time required to reach the target minimum dosage (E.g., 25 mJ/cm^2). The experimentation indicated that high proximity may not be effective at coverage (see circular gradient), but has very high dosage rate (rates of 20 mJ/cm^2/min plus), shows an increase of 2100% increase in dosage.

The term "connected" or "coupled to" may include both direct coupling (in which two elements that are coupled to each other contact each other) and indirect coupling (in which at least one additional element is located between the two elements).

Although the embodiments have been described in detail, it should be understood that various changes, substitutions and alterations can be made herein without departing from the scope. Moreover, the scope of the present application is not intended to be limited to the particular embodiments of the process, machine, manufacture, composition of matter, means, methods and steps described in the specification.

As one of ordinary skill in the art will readily appreciate from the disclosure, processes, machines, manufacture, compositions of matter, means, methods, or steps, presently existing or later to be developed, that perform substantially the same function or achieve substantially the same result as the corresponding embodiments described herein may be utilized. Accordingly, the appended claims are intended to include within their scope such processes, machines, manufacture, compositions of matter, means, methods, or steps.

As can be understood, the examples described above and illustrated are intended to be exemplary only.

The invention claimed is:

1. A system for sterilizing a plurality of cylindrical gaming tokens positioned in parallel rows within one or more corresponding apertures within a gaming token tray, the system comprising:

a gaming token tray lid housing including a sterilizing light emitter, which when activated, causes a sterilizing light to be emitted within the housing, the gaming token tray lid housing including an electrical contact that completes an electrical circuit when the gaming token tray lid housing is positioned on a corresponding gaming token tray;

the gaming token tray having the one or more corresponding apertures, each aperture configured to receive a row of cylindrical gaming tokens of the plurality of cylindrical gaming tokens, the gaming token tray comprising:

a plurality of modular roller devices, each modular roller device of the plurality of modular roller devices configured to be positioned between two adjacent parallel rows of cylindrical gaming tokens or an adjacent parallel row of cylindrical gaming tokens and a sidewall of the gaming token tray, each modular roller device comprising:

one or more rollers adapted to be in physical contact with adjacent cylindrical gaming tokens in the adjacent parallel row or rows such that the one or more rollers, when rotated, cause the adjacent cylindrical gaming tokens to rotate through frictional engagement;

one or more actuators coupled to a corresponding roller or corresponding rollers of the one or more rollers, which when electrically activated, cause the corresponding roller or corresponding rollers to rotate; and a controller circuit having at least one computer processor and coupled to the one or more actuators that cause rotation of the one or more rollers of the modular roller device for a duration of time such that the cylindrical gaming tokens are also rotated for the duration of time wherein the controller circuit includes one or more load sensor circuits configured to generate load data based at least on a corresponding rotation speed of each of the one or more rollers and a corresponding amount of power or energy provided to the one or more actuators, the load data provided to a central computer server coupled to each of the plurality of modular roller devices.

2. The system of claim 1, wherein the central computer server is configured to monitor the load data and to generate an alert when the load data corresponding to a modular roller device of the plurality of modular roller devices indicates an abnormal operating condition.

3. The system of claim 2, wherein the each of the one or more corresponding apertures within the gaming token tray includes one or more object detection sensors configured for tracking a load level corresponding to the corresponding aperture, and the abnormal operating condition is determined based on the load level of the adjacent row or the adjacent rows of the modular roller device corresponding to the load sensor.

4. The system of claim 1, wherein the controller circuit is configured to, upon detecting completion of the electrical circuit when the gaming token tray lid is positioned on the gaming token tray, control the one or more actuators to actuate for the duration of time.

5. The system of claim 4, wherein the electrical circuit is completed through electrical coupling of two sets of corresponding two or more power pins residing on the gaming token tray lid or the gaming token tray, respectively.

6. The system of claim 1, wherein the gaming token tray lid housing includes a timing circuit configured to control the duration of time in which the sterilizing light emitter is activated.

7. The system of claim 6, wherein the timing circuit is coupled to at least one controller circuit of at least one modular roller device and configured to modify the duration of time based on the load data received from the at least one modular roller device.

8. The system of claim 1, wherein the one or more corresponding apertures have an elliptical profile such that the cylindrical gaming tokens positioned within the one or more corresponding apertures are biased towards a bottom of the one or more corresponding apertures to increase a frictional engagement between the one or more rollers and the cylindrical gaming tokens.

9. The system of claim 1, wherein the plurality of modular roller devices are configured as removable modular inserts that are inserted into corresponding channels in the gaming token tray and electrically coupled to a power source residing within or proximate to the gaming token tray.

10. The system of claim 1, wherein the controller circuit is further configured to receive token presence data from a plurality token detection modules, each token detection module comprising a plurality of photoemitter/photoreceptors pairs configured for determining a presence of a corresponding cylindrical gaming token disposed within a corresponding location in the aperture.

11. The system of claim 10, wherein the token presence data is utilized by the controller circuit to determine an expected load value associated with operation of the one or more rollers.

12. The system of claim 10, wherein the token presence data is utilized by the controller circuit to maintain, in a data structure, one or more data objects representing whether tokens residing in one or more physical zones within the one or more apertures have been interacted with since a last sterilization cycle.

13. The system of claim 12, wherein each of the one or more physical zones is associated with a minimum sterilization duration based at least on a distance from the sterilizing light emitter during operation of a sterilization cycle, and the controller circuit sets the duration of time for operating the one or more rollers based on a maximum of the minimum sterilization durations for all zones of the one or more physical zones that have been interacted with since the last sterilization cycle.

14. The system of claim 13, wherein the distance from the sterilizing light emitter is based at least on a vertical distance arising from a slope in positioning of the one or more apertures.

15. The system of claim 10, wherein each modular roller device further comprises the plurality of photoemitter/photoreceptors pairs configured operating in conjunction with the one or more rollers.

16. The system of claim 10, wherein each modular roller device is disposed to alternate with a plurality of token detection modules.

17. The system of claim 1, wherein the one or more rollers are configured for limited translational motion along an axis of extension or retraction.

18. The system of claim 17, wherein the limited translational motion along the axis includes an active biasing force controlled by the controller circuit to increase engagement with the cylindrical gaming token, the active biasing force based at least on feedback forces from the cylindrical gaming token.

19. The system of claim 17, wherein the limited translational motion along the axis includes a passive biasing force controlled by the controller circuit to increase engagement with the cylindrical gaming token, the passive biasing force provided by a spring.

* * * * *